US007989555B2

(12) United States Patent
Kodali

(10) Patent No.: US 7,989,555 B2
(45) Date of Patent: Aug. 2, 2011

(54) GLYCEROL DERIVATIVES AND METHODS OF MAKING SAME

(75) Inventor: Dharma R. Kodali, Plymouth, MN (US)

(73) Assignee: Global Agritech, Inc., Minneapolis, MN (US)

( * ) Notice: Subject to any disclaimer, the term of this patent is extended or adjusted under 35 U.S.C. 154(b) by 334 days.

(21) Appl. No.: 11/751,432

(22) Filed: May 21, 2007

(65) Prior Publication Data

US 2008/0293602 A1    Nov. 27, 2008

(51) Int. Cl.
*C08G 63/02*   (2006.01)
*C08G 18/48*   (2006.01)
*C08L 75/00*   (2006.01)

(52) U.S. Cl. ............ 525/437; 524/590; 522/65; 522/91; 525/127

(58) Field of Classification Search .................. 554/213; 560/129, 190; 252/182.21, 182.22, 182.27, 252/182.13; 528/76, 28, 44, 65, 75, 85, 301; 260/75; 522/90–97, 174; 524/507, 588, 524/589, 590, 595; 525/123, 127, 455; 526/302
See application file for complete search history.

(56) References Cited

U.S. PATENT DOCUMENTS

| | | | |
|---|---|---|---|
| 3,032,971 A | | 5/1962 | Shotton |
| 3,671,471 A | * | 6/1972 | Jamison .......................... 521/77 |
| 4,503,252 A | | 3/1985 | Felder et al. |
| 4,610,696 A | * | 9/1986 | Bernasconi et al. ............ 44/443 |
| 5,308,365 A | | 5/1994 | Kesling, Jr. et al. |
| 5,578,090 A | * | 11/1996 | Bradin ............................ 44/308 |
| 5,710,350 A | | 1/1998 | Jeromin et al. |
| 5,998,669 A | | 12/1999 | Klix et al. |
| 6,093,786 A | | 7/2000 | Kelsey |
| 6,465,401 B1 | | 10/2002 | Kodali et al. |
| 6,531,636 B1 | | 3/2003 | Mechoulam et al. |
| 6,602,963 B2 | * | 8/2003 | Siol et al. ....................... 525/437 |
| 6,890,364 B2 | | 5/2005 | Delfort et al. |
| 2001/0041659 A1 | * | 11/2001 | Becker et al. .................. 504/140 |
| 2003/0232729 A1 | * | 12/2003 | Beilfuss et al. ................ 508/579 |
| 2004/0204560 A1 | * | 10/2004 | Chen et al. ..................... 528/272 |

FOREIGN PATENT DOCUMENTS

WO    WO 99/51560    10/1999

OTHER PUBLICATIONS

Sorenson, Wayne R. and T.W. Campbell, "Preparative Methods of Polymer Chemistry", Interscience Publishers, New York, 1961.
http://www.shellchemicals.com/corterra/1, 1098, 1091, 00.html, "Corterra Polymer 9200". © 2006, Shell Chemicals Limited.
Reddy, K.R. et al., "Copper(II)-Promoted Regioselective Synthesis of 1,4-Disubstituted 1,2,3-Triazoles in Water", *Synlett* 2006, No. 6, pp. 957-959.
Orthoefer, Frank T., "Performance of trans-free vegetable oils in shortenings and deep-fat frying", *Lipid Technology*, vol. 17, No. 5, May 2005, pp. 101-106.
Kolb H.C. and Sharpless K.B., "The Growing impact of click chemistry on drug discovery", www.drugdiscoverytoday.com, vol. 8, No. 24, Dec. 2003, pp. 1128-1137.

Kodali, D.R., "High Performance ester lubricants from natural oils", *Industrial Lubrication and Tribology*, vol. 54, No. 4, 2002, pp. 165-170.
Klepacova, K. et al., "*tert*-Butylation of glycerol catalysed by ion-exchange resins", Applied Catalysis A:General 294, Elsevier B.V. © 2005, pp. 141-147.
Kantam et al., "Nanocrystalline ZnO as an Efficient Heterogeneous Catalyst for the Synthesis of 5-Substituted 1*H*-Tetrazoles", *Adv. Synth. Catal.*, vol. 347, 2005, pp. 1212-1214.
Kantam et al., "An efficient synthesis of 5-substituted 1H-tetrazoles using Zn/a; Hydrotalcite catalyst", *Journal of Molecular Catalysis A:Chemical* 247, 2006, pp. 186-188.
Clacens, J. M. et al., "Selective etherification of glycerol to polyglycerols over impregnated basic MCM-41 type mesoporous catalysts", *Applied Catalysis A: General* 227, 2002, pp. 181-190.
Chuah, Hoe H., Crystallization Kinetics of Poly (Trimethylene Terephthalate) , *Polymer Engineering and Science*, Feb. 2001, vol. 41, No. 2, pp. 308-313.
Chittenden, Gordon J.F., "Selective alkylation of glycerol: direct synthesis of 2-0-benzylglycerol and 2-0-methylglycerol", *Carbohydrate. Research*, vol. 91, 1981, pp. 85-88.
http://www.ag.iastate.edu/centers/ccur/biorenewables/publications/fattyacidoverview0105/f.., Bozell, Joe, "Oleochemicals as a Feedstock for the Biorefinery: High Value Products From Fats and Oils", National Renewable Energy Laboratory, Aug. 18, 2004, pp. 1-28.
Achilias, D.S. et al., Isothermal and Nonisothermal Crystallization Kinetics of Poly(propylene terephthalate), *Journal of Polymer Science: Part B: Polymer Physics*, vol. 42, pp. 3775-3796 (2004).
Wang et al., "Conversion of Glycerol to 1, 3-Propanediol via Selective Dehydroxylation", *Ind. Eng. Chem. Res.*, 2003, 42, pp. 2913-2923.
Stevens, E.S. "What Makes Green Plastics Green?", *BioCycle*, Mar. 2003, pp. 24-27.
Smith, James G. et al., "Preparation and Properties of Poly(methylene terephthalates)", *Journal of Polymer Science: Part A-1*, vol. 4, 1966, pp. 1851-1859.
Roupakias, C.P. et al., "Synthesis, Thermal Characterization, and Tensile Properties of Alipharomatic Polyesters Derived from 1,3—Propanediol and Terephthalic, Isophthalic, and 2,6-Naphthalenedicarboxylic Acid",*Journal of Polymer Science: Part A: Polymer Chemistry*, vol. 43, 2005, pp. 3998-4011.
Ward, I.M. et al., "The Mechanical Properties and Structure of Poly(m-methylene Terephthalate) Fibers", *Journal of Polymer Science; Polymer Physics Edition*, vol. 14, 2006, pp. 263-274.
"Click Chemistry: A Click Away from Discovery", © 2007 Sigma-Aldrich Co., 3 pp.
Ye, Su, www.mda.state.mn.us, "Economic Impact of Soy Diesel in Minnesota", Sep. 2006, 5 pp.
www.corterra.com, "1,3-Propanediol", © 2002 Shell Oil/Shell Chemical LP, 8 pp.
Muska, Carl F. and Alles Carina, "Biobased 1,3-Propanediol—A New Platform Chemical for the 21st Century", *BioPerspectives 2005*, BREW Symposium, May 11, 2005, pp. 1-38.

* cited by examiner

Primary Examiner — Ellen M McAvoy
Assistant Examiner — Pamela Weiss

(57) ABSTRACT

Symmetrical polyols, polyol esters, polyesters, polyurethanes, triazoles, and polyvinylethers derived from glycerol and methods of making the symmetrical polyols, polyesters, polyurethanes, polyhydroxyvinylethers and triazoles are discussed. Also provided is a method of making serinol.

14 Claims, No Drawings

GLYCEROL DERIVATIVES AND METHODS OF MAKING SAME

CROSS-REFERENCE TO RELATED APPLICATION(S)

None

FIELD OF THE INVENTION

The present invention relates generally to synthesis of symmetrical polyols and their derivatives from glycerol. The invention further relates to making polyesters and polyurethanes from symmetrical polyols suitable for various industrial applications.

BACKGROUND OF THE INVENTION

Glycerol is a trihydric alcohol, 1,2,3-propanetriol, and has been known to mankind since the late $18^{th}$ century. Since its discovery from fats and oils it has been used in a number of applications, which extend to the thousands. The major current uses of glycerol include food, cosmetics, pharmaceuticals, plastics, toothpaste, urethane foam, explosives, synthetic resins, ester gums and other miscellaneous applications.

One process of producing glycerol has water and fat fed into a splitting column under pressure (up to 6 Mpa) and above 220° C. leading to a 15% solution of crude glycerol and fatty acid. This crude glycerol is further purified and distilled to make it into a pharmaceutical grade. The glycerol that results from fat splitting is a natural glycerol and if the oil used is of vegetable origin, it could be of kosher grade.

The major user of fatty acids from fat splitting is the soaps and detergents industry. Therefore, the glycerol production varies depending upon the soap demand.

Glycerol is also manufactured from various streams of petroleum products like glycidol and epichlorohydrin. Petroleum derived glycerol is a synthetic glycerol and is declining in volume. Glycerol production from fermentation is another emerging technology but currently has limited scope.

Major derivatives of glycerol include esters, acetals, ethers and amines. Alkyd resins use glycerol and phthalic anhydride. Various partial glycerol fatty acid esters are used as food emulsifiers in large quantities.

One of the major derivatives of glycerol is polyglycerols. Polyglycerols are ether oligomers produced by self-condensation of glycerol. Polyglycerols and their derivatives are extensively used in industrial, food and cosmetic applications. For example, polyglycerol esters function as emulsifiers, dispersants, spreading agents, flavor or fragrance carriers, rheology modifiers, solubilizers and emollients.

One type of commercial production process of polyglycerol employs alkaline condensation of glycerol. One of the important members of polyglycerols is diglycerol. Other commercial production processes are more directed condensation process by reacting glycerol with epichlorohydrin, followed by hydrolysis, neutralization and purification. These other processes lead to a higher purity diglycerol. Desirable diglycerol properties include solubility in water and aqueous systems, compatibility with electrolytes, biocompatibility as it is recognized by skin components for various cosmetics applications, high hydrogen bonding propensity, imparting humectant properties to the product, high hydroxyl value which acts as a crosslinking agent in a variety of applications including the formation of gels, no reactivity with the active components of the formulation and environmental compatibility, as it readily biodegrades.

The worldwide production of glycerol is currently about 900 thousand tons/year. Roughly 20% of this volume is produced in United States. Most of the glycerol, about 90%, is produced from fats and oils from fat/oil splitting during fatty acid production. In the last decade, due to the improved worldwide economy, the demand for soaps increased thereby increasing fat splitting and glycerol production.

Additionally, in the past two decades the developmental efforts to use fats and oils and their by products for other industrial applications has increased considerably. This is partially driven by the "green" image perceived by the public and the environmental benefits associated with the use of renewable raw materials.

Biodiesel fuel is an alternative product that has been developed and is supported by the recent higher prices of petroleum-based products and the desire to reduce the dependency on foreign petroleum. The benefits of environmentally acceptable products include lower pollution (air, water and soil), and minimal health and safety risks. Also, there are some legislative incentives and requirements that are prodding industries to move towards less polluting and environmentally friendly products. In spite of all these drivers, the use of industrial products is primarily dictated by cost and performance.

Biodiesel fuel is produced by transesterification of fat/oil with methanol. Typically a base catalyst is used to facilitate the transesterification. A typical mass balance of this reaction—about 100 lbs of vegetable oil will react with about 10 lbs of methanol and a fraction of a lb of sodium methoxide (catalyst) to yield about 100 lbs of biodiesel fuel and 10 lbs of glycerol. However, the yields and quality of the output depends upon the feedstock.

Increased biodiesel fuel production worldwide has dampened the prices of glycerol. It is theorized that in the United States alone if the production of biodiesel fuel reaches a billion gallons/year, it will increase the glycerol production by 200%. This increased glycerol production volume will glut the market and likely drop the prices to less than half of the current level.

Therefore, a need exists for using the glycerol from increased production to benefit industry. Additionally, using glycerol based products will be economically advantageous based on the large supply of glycerol and potentially low cost of glycerol.

BRIEF SUMMARY OF THE INVENTION

The present invention surprisingly provides symmetrical polyols from glycerol and includes methods of making and utilizing the same, which are suitable for various industrial applications. The symmetrical polyols and their derivatives of the present invention are prepared from glycerol.

In one embodiment compounds are a mono or diester including

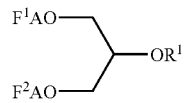

wherein $F^1A$ and $F^2A$ are each independently a fatty acid residue or a hydrogen atom, but not both hydrogen atoms, and $R^1$ is an alkyl group or alkylene ether containing ester.

In some embodiments $F^1A$ or $F^2A$ are each independently a C2 to C24 linear or branched fatty acid residue containing zero to three double bonds.

In one aspect, $F^1A$ or $F^2A$ are each independently a C6 to C24 linear or branched fatty acid residue containing zero to three double bonds.

In some embodiments $F^1A$ or $F^2A$ are mixtures of fatty acid residues from palm oil, peanut oil, cottonseed oil, soybean oil, canola oil, corn oil, sunflower oil or other triacylglycerols containing oils such as jatropha.

In another embodiment $F^1A$ and $F^2A$ are mixtures of fatty acid residues from palm olein.

In yet another embodiment $F^1A$ and $F^2A$ are both an 2-ethylhexanoic acid ester residue.

In one aspect, a lubricant composition includes a mono or diester including:

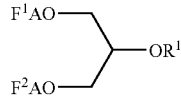

wherein $F^1A$, $F^2A$ and $R^1$ are as previously defined.

In another aspect, the lubricant composition includes at least one additive including viscosity-index improvers, pour point depressants, oxidation inhibitors, anti-wear agents, anti-foam additives, corrosion inhibitors, dispersants, detergents, acid neutralizers, rust inhibitors or combinations thereof.

In yet another aspect, a lubricant composition comprising the formula

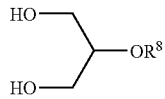

wherein $R^8$ is a methyl, ethyl, propyl, butyl, pentyl or hexyl group, and at least one additive comprising viscosity-index improvers, pour point depressants, oxidation inhibitors, anti-wear agents, anti-foam additives, corrosion inhibitors, dispersants, detergents, acid neutralizers, rust inhibitors or combinations thereof.

Another embodiment of the present invention includes a method to prepare

(compound I, serinol)

including the steps of
converting the hydroxyl of compound (II)

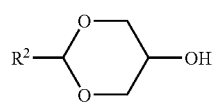 (II)

to a leaving group (L) to afford compound (III),

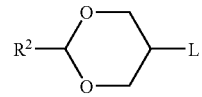 (III)

treating compound (III) under conditions wherein L is replaced by an azide to afford compound (IV)

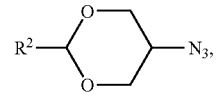 (IV)

subjecting compound (IV) to a reducing agent to reduce the azide of compound (IV) to an amine compound (V)

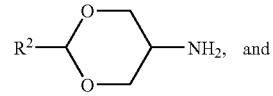 (V)

subjecting compound (V) to conditions suitable to afford compound (I), wherein $R^2$ is an alky or aryl group, and L is a leaving group.

In one aspect, $R^2$ is a phenyl group.

In another aspect, L is a tosyl group.

In one embodiment the reducing agent is lithium aluminum hydride.

In another embodiment the last step is under acidic conditions.

In one embodiment the compounds have the formula:

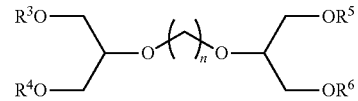

wherein $R^3$, $R^4$, $R^5$, $R^6$ are each independently a hydrogen, an alkyl, —C(=O)$R^{18}$ group or combinations thereof, provided when one or more $R^3$, $R^4$, $R^5$, $R^6$ is —C(=O)$R^{18}$, then each $R^{18}$ independently is an alkyl group; and wherein n is 1 to 16, in particular n is 2 to 6.

In another embodiment the compounds have the formula:

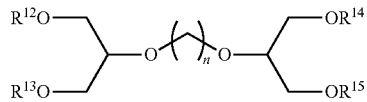

wherein $R^{12}$, $R^{13}$, $R^{14}$, $R^{15}$ are each independently a methacrylate, acrylate, vinyl ether or combinations thereof, and wherein n is 1 to 16, in particular n is 2 to 6.

In yet another embodiment $R^{12}$, $R^{13}$, $R^{14}$ or $R^{15}$ further includes at least one alkyl containing group or —C(=O)$R^{18}$ group, wherein each $R^{18}$ independently is an alkyl group.

In some embodiments, a polyester is the condensation product of one or more of a diacid, a diacid halide, or a diester and

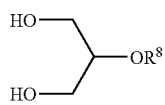

wherein $R^8$ is an alkyl group.

In another embodiment, the diacid is $HOOC(CH_2)_n COOH$, wherein n is 0 to 20, in particular n is 2 to 8.

In one aspect, $R^8$ is a methyl, ethyl, propyl, butyl, pentyl or a hexyl group.

In another aspect, the molecular weight of the polyester is greater than about 500 grams/mole, in particular between about 500 and about 100,000, and more particularly between about 1,000 to 80,000.

In yet another aspect, a terminal hydroxyl group of the polyester is derivatized with a methacrylate, an acrylate, a hydrolysable alkoxysilane, a photo initiator or combinations thereof.

In some embodiments, a crosslinked polyester is the condensation product of one or more of a diacid, a diacid halide, or a diester with a tetrol having the formula

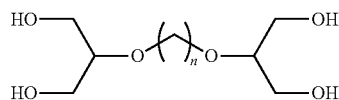

wherein n is 1 to 16, in particular n is 2 to 6.

In some embodiments, a crosslinked polyester is a condensation product of one or more of a diacid, a diacid halide, or a diester, with a tetrol having the formula

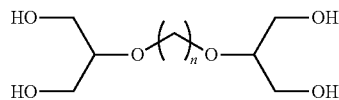

wherein n is 1 to 16, in particular n is 2 to 6, and a diol.

In some embodiments polyurethanes of the present invention are the condensation product of a diisocyanate and

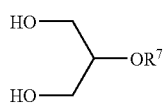

wherein $R^7$ is an alkyl, substituted alkyl, aryl or substituted aryl group.

In one aspect, $R^7$ is methyl, ethyl, propyl, butyl, pentyl or hexyl group.

In another aspect, the molecular weight of the polyurethane is greater than about 500 grams/mole, in particular between about 500 and about 150,000, and more particularly between about 1,000 to 100,000.

In some embodiments the hydroxyl group of the polyurethane is derivatized with a methacrylate, an acrylate or a vinyl ether or hydrolysable alkoxysilanes or a photoinitiator.

In one embodiment a crosslinked polyurethane of the present invention is the condensation product of a diisocyanate and a tetrol having the formula

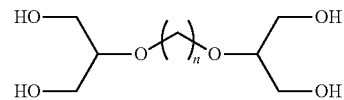

wherein n is 1 to 16, in particular n is 2 to 6.

In some embodiments a crosslinked polyurethane which is a condensation product of diisocyanate and a tetrol having the formula

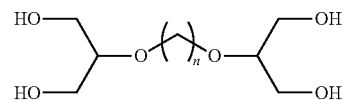

wherein n is 1 to 16, in particular n is 2 to 6, and a diol.

The invention further includes methods of making polyurethanes described herein.

In some embodiments a compound including the formula:

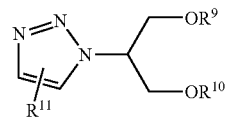

wherein $R^9$ and $R^{10}$ are each independently a hydrogen, an alkyl group or an aryl group, and $R^{11}$ is an alkyl group, an aryl group or combinations thereof.

In another embodiment a compound including the formula:

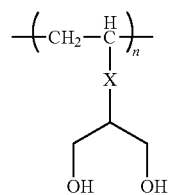

wherein n is greater than 10, in particular n is 10 to 100,000, more particularly, n is 20 to 50,000 and wherein X is $-O-$, $-O-CH_2CH_2-O-$, $-CONH-$ or $-COO-$.

In another embodiment, a fuel composition including gasoline, diesel fuel or biodiesel used in internal combustion engine and at least one glycerol ether including the formula:

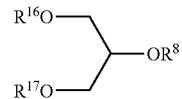

wherein $R^{16}$ and $R^{17}$ are each independently a hydrogen or $-C(=O)R^{18}$ group, provided when one or more $R^{16}$, $R^{17}$ is $-C(=O)R^{18}$, then each $R^{18}$ independently is an alkyl group; and $R^8$ is an alkyl group.

In yet another embodiment, $R^8$ is an alkyl group and $R^{16}$ and $R^{17}$ are hydrogen.

In some embodiments, $R^{16}$, $R^{17}$ and $R^8$ are each independently an alkyl group.

In one aspect, the diesel fuel is from petroleum.

In another aspect the biodiesel is a mixture of fatty acid alkyl esters from fats and oils.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION OF THE INVENTION

The present invention pertains to symmetrical polyols synthesized from glycerol and methods of synthesizing symmetrical polyols from glycerol suitable for various industrial applications. The symmetrical polyols and their derivatives of the present invention are prepared from glycerol.

Using glycerol based products will have economical advantage because of the growing supply of glycerol and the potential low cost of glycerol.

The commodity crop production in the United States is burdened by overproduction and is sustained by government subsidies. The global competitiveness and overproduction of fats and oils is also evident worldwide. The total production of vegetable oils is more than doubling in volume for every 20 to 25 years. For example, the total annual production of fats and oils around the world grew from 53 million metric tons (MMT) in 1980 to current production of more than 136 MMT/year. By conservative estimates this production growth is expected to surpass 175 MMT by 2020. The current United States fats and oils production is about 14 MMT/year. More than 25% production is available for non-food applications and export. These factors strongly support the development of alternate products from vegetable oils that provide new and value added markets. Biodiesel is one such alternate product that has been developed in commercial quantities and experimented as a biofuel in the past decade.

The life cycle analysis shows that renewable biodiesels do not add any net carbon dioxide to the atmosphere. Diesel is one of the primary fuels used for transportation in US, with an annual consumption of about 55 billion gallons/year. It is highly unlikely any single other source of fuel can substitute diesel to any large extent. Ethanol blends in gasoline, E10 (10% ethanol in gasoline) as an oxygenated fuel has been used for the past 20 years. Similarly, biodiesel blends of B2 to B20 (2-20% biodiesel in diesel) are being experimented in various states. Minnesota is the only state in which B2 fuel is mandatory since September 2005. A number of states including Arkansas, Indiana, and Iowa are offering production linked incentives for biodiesel use.

As a transportation fuel up to B20 levels biodiesel is a "drop in" and do not require any engine modifications. A number of studies have shown that the biodiesel decreases the carbon monoxide (CO), particulate matter in the exhaust, and improves the lubricity and there by increasing engine efficiency. The improved lubricity of biodiesel is particularly useful in view of the new regulations that require the reduction/elimination of sulfur in the diesel resulting in increased fuel pump wear and breakdown. It also enhances the cetane number (a measure of the combustibility of diesel fuel) and reduces the pollution, which is especially beneficial in densely populated urban areas.

Biodiesel is produced by transesterification of fat/oil with methanol. Typically a base catalyst is used to facilitate the transesterification. A typical mass balance of this reaction—about 100 lbs of vegetable oil will react with about 10 lbs of methanol and fraction of a lb of sodium methoxide (catalyst) to yield about 100 lbs of biodiesel and 10 lbs of glycerol. However the yields and quality of the output depends upon the feedstock.

The majority of the cost (80%) of the biodiesel production is the cost of the feedstock. There are two main categories of feedstock that are available, one vegetable oil based and the other animal fat based. In the vegetable oil based materials soybean oil is the most cost effective, followed by canola oil and others. Biodiesel production from the used vegetable oils (recycled) is difficult to process, but is more cost effective. The potential excess vegetable oil available in United States can produce about 500 million gallons of biodiesel (consuming roughly 2 MMT of fats and oils).

Vegetable oil based biodiesel fuels have good low temperature properties, such as low cold filtration plugging point temperatures, and are better suited to be used in the colder climates. The animal fats, both edible and non-edible, are cheaper feedstock than vegetable oils. The animal fat derived biodiesel due to saturated fatty acid composition have higher cold filter plugging point temperatures and will not be suitable for use in cold climates or in higher blend concentrations. If a technical solution could be found to improve the cold flow properties for the animal fat based biodiesel, it will become a lot more economically attractive.

The current potential for animal fat based biodiesel is more than 500 million gallons/year. If Bovine Spongiform Encephalopathy ("mad cow disease") regulations come into effect, then this situation can add another 1.2 billion gallons of animal fat based biodiesel to the market. In developing countries some indigenous vegetable oil feed stocks from the crops that can be grown in the semi-arid regions are being developed for biodiesel production. Jatropha oil is one example of indigenous feed stock.

The economics of biodiesel production depends upon the cost of the feedstock, glycerol credit (price) and the operating expenses. The operating expenses are, for the most part, very similar and approximate to 50 U.S. cents/gallon. For example at 20 U.S. cents/lb-soybean oil, 8 lbs of oil can generate a gallon of biodiesel costing about USD 2.10 as of May 2007.

The term glycerol is commonly known as glycerin and these two terms are used interchangeably. The glycerin from the vegetable oil origin is considered kosher and demands a premium, where as animal fat derived glycerin is not. From the above example it is clear at the current, May 2007, diesel prices of about USD 2/gallon, biodiesel from vegetable oil has comparable cost.

In October 2004, the United States Congress passed the American Jobs Creation Act providing federal excise tax credit or payment for biodiesel. This incentive provides a credit or payment of USD 1.00/gallon for agri-biodiesel or a USD 0.50/gallon for the biodiesel other than agri-based or used. Now with the government incentive, the biodiesel example from vegetable oil discussed above will become cheaper than diesel and will be more attractive to both producers and consumers. This incentive scenario enhanced the future biodiesel production capacity enormously. Annual capacity of biodiesel increased from a mere 0.5 million gallons in 1999 to 20 million gallons in 2003. Two years later, biodiesel capacity more than tripled to 75 million gallons per year, and more than tripled again between 2005 and 2006, to more than 575 million gallons per year. In the next few years, by some estimates, the biodiesel demand will increase to at least one billion gallons/year.

It is expected that a similar trend in the world wide production of biodiesel may result in about 4 billion gallons of biodiesel consuming about 15 MMT of fats and oils (<10% of total fats and oils/year). This will result in about two million tons of glycerol more than two times the current production into the market.

Currently, May 2007, about 900 thousand tons/year of glycerol is produced worldwide, out of which the US produces close to 200 thousand tons. About 90% of the glycerol comes from fat/oil splitting during the fatty acid production. Within the last decade due to the improved worldwide economy, the demand for soaps increased thereby increasing fat splitting and glycerol production. This coupled with increased biodiesel production worldwide dampened the prices of glycerol from USD 1.00/lb to 50 U.S. cents/lb as of May 2007. Now the new tax incentive scenario will further increase the biodiesel and glycerol production. The biodiesel tax incentive is also being considered or offered in European countries, India, Australia and others. Europe and other countries are promoting biodiesel production and use.

In the United States alone if the production of biodiesel reaches a billion gallons/year, it will increase the glycerol production by 200%. This increased glycerol production volume will glut the market and likely drop the prices to less than half of the current level. In turn, this drop in glycerol price will reduce the glycerol credit for the biodiesel production and reduce its economic viability. The potential production of 4 billion gallons of biodiesel world-wide will result in two million tons of additional glycerol production. This is more than two times increase in glycerol production and will drop the price from the current, May 2007, 50-60 U.S. cents/lb to 20-30 U.S. cents/lb. However it is expected that the glycerol price may stabilize at 15-20 U.S. cents/lb as this can support the high volume applications like animal feed and fermentation.

Glycerol value added products from the present invention will expand the glycerol markets and improve the price of glycerol.

Additional advantages of using the symmetrical polyols of the present invention include molecular symmetry and bifunctionality that impart unique physical and functional properties due to high purity and single molecular structure. Also, the hydroxyl groups present are primary, making them more reactive. This feature helps to differentiate from the other glycerol derivatives as there is no secondary hydroxyl which is less reactive or prone to oxidation.

The β-hydrogen in the symmetrical polyols is ether-linked hydrogen compared to an ester, making it less susceptible to oxidation. This will enhance the oxidative stability of the resulting products.

The glycerol used for the production of polymers in the present invention are from biorenewable feedstock. Besides superior performance and cost, other advantages including sustainability, renewability, ready biodegradability, green chemistry and industrial ecology are guiding the development of the next generation of materials, products, and processes. The current ecological concerns are forcing the development of environmentally benign and sustainable materials and fuels. Biodegradable plastics polymer products based on annually renewable agricultural feedstock can provide a portfolio of sustainable, eco-efficient products that can compete and capture markets currently dominated by products based on petroleum feedstock. Many of these new materials are derived from plant materials such as corn, potatoes, biomass and vegetable oils.

Glycerol, a prime example of green material, is a byproduct of vegetable oil processing to soaps and biodiesel, which can be modified to make polymers and other industrial applications. The synthesis of polymeric materials based on monomer from renewable feedstock is a steadily growing field of interest. Many of these monomers have unique structures which are not available from conventional sources. Therefore, new and interesting material properties can be obtained with regard to thermal and Theological behavior. In addition, the use of renewable feedstock is stimulated by the growing concern for the environment and the rapid depletion of the mineral oil reserves. Renewable monomers with a large functional diversity are already available from a wide range of resources. Improved production processes to obtain various bio-based monomers on large scales as well as the development of a sustainable economy should make the use of monomers from renewable feedstock even more economically attractive in the future. A prime example of a green material is glycerol. Glycerol is a byproduct of vegetable oil processing into soaps and biodiesel, which can be modified to make it suitable for polymers and other industrial applications.

The symmetrical polyols of the present invention and their derivatives are useful in number of commercial applications. Some of these intended applications are lubricants, coatings, cosmetics, polyurethanes, polyesters, and various emulsifier and surfactants such as non-ionic surfactants. Furthermore, reacting the symmetrical polyols of the present invention with isocyanates produce flexible and rigid polyurethane foams.

The term "polyol" refers to a compound comprising two or more hydroxyl groups.

In the specification and in the claims, the terms "including" and "comprising" are open-ended terms and should be interpreted to mean "including, but not limited to . . . ." These terms encompass the more restrictive terms "consisting essentially of" and "consisting of."

A) Mono and Diesters of Glycerol Ethers

Compounds of the present invention include the 2-alkyl glycerol monoesters of fatty acids outlined in the Examples Section below. These examples include synthesis of palm olein fatty acid mono-ester of 2-methyl glycerol (Compound 8), synthesis of palm olein fatty acid mono-ester of 2-ethyl glycerol (Compound 9), and synthesis of palm olein mono-ester of 2-propyl glycerol (Compound 10).

The mono or diester compounds of the present invention include

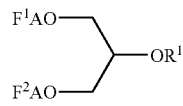

wherein $F^1A$ and $F^2A$ are each independently a fatty acid residue or a hydrogen atom, but not both hydrogen atoms, and $R^1$ is an alkyl group or alkylene ether containing ester.

In particular, $F^1A$ or $F^2A$ are each independently a C2 to C24 linear or branched fatty acid residue containing zero to three double bonds. More particularly, $F^1A$ or $F^2A$ are each independently a C6 to C24 linear or branched fatty acid residue containing zero to three double bonds.

In some embodiments $F^1A$ or $F^2A$ are mixtures of fatty acid residues from palm oil, peanut oil, cottonseed oil, soybean oil, canola oil, corn oil, sunflower oil or other triacylglycerols containing oils such as jatropha.

In another embodiment $F^1A$ and $F^2A$ are mixtures of fatty acid residues from palm olein.

In yet another embodiment $F^1A$ and $F^2A$ are both an 2-ethylhexanoic acid ester residue.

Palm olein is the liquid fraction of palm oil.

TABLE 1

Analysis of Palm Oil and Palm Olein

| Property | Palm Oil | Palm Olein |
|---|---|---|
| Free Fatty acid | 0.074 | 0.095 |
| Moisture and Impurities | 0.035 | 0.036 |
| Iodine Value | 52.7 | 56.96 |
| Melt point | 35.8° C. | 22.2° C. |
| Cloud point | — | 7.5° C. |
| Color | 2.9 red | 2.9 red |

TABLE 2

Fatty Acid Composition of Palm Oil and Palm Olein

| Fatty Acid | Palm Oil | Palm Olein |
|---|---|---|
| C12:0 | 0.23 | 0.2 |
| C14:0 | 1.09 | 1.0 |
| C16:0 | 44.0 | 39.8 |
| C18:0 | 4.54 | 4.4 |
| C18:1 | 39.15 | 42.5 |
| C18:2 | 10.12 | 11.2 |
| C18:3 | 0.37 | 0.4 |
| C20:0 | 0.38 | 0.4 |
| Average Molecular Weight | 284 | 285.7 |

Fats and oils are triesters of glycerol (triacylglycerols). The carboxylic acid obtained from the hydrolysis of a fat or oil is called a fatty acid. Fatty acids generally have long, unbranched saturated and unsaturated hydrocarbon chains.

Fatty acids include saturated fatty acids such as butyric acid ($CH_3(CH_2)_2CO_2H$), palmitic acid ($CH_3(CH_2)_{14}CO_2H$) and stearic acid ($CH_3(CH_2)_{16}CO_2H$), unsaturated fatty acids such as oleic acid ($CH_3(CH_2)_7CH=CH(CH_2)_7CO_2H$), and polyunsaturated fatty acids such as linoleic acid ($CH_3(CH_2)_4CH=CHCH_2CH=CH(CH_2)_7CO_2H$) and linolenic acid ($CH_3CH_2CH=CHCH_2CH=CHCH_2CH=CH(CH_2)_7CO_2H$).

Fats and oils contain more than one type of fatty acid. For example, corn oil includes palmitic, stearic oleic and linoleic fatty acids and soybean oil includes palmitic, stearic, oleic, linoleic and linolenic fatty acids.

The primary properties required for bio-based esters are low temperature fluidity and oxidative stability. These two properties are directly related to the nature of fatty acids and the composition that depends on the type of vegetable oil or animal fat they derived from.

In general the saturated fatty acid esters, like palmitic and stearic acid esters are oxidatively more stable but have poor low temperature properties. The polyunsaturated fatty acid esters, like linoleic and linolenic acid esters, provide good low temperature flow properties but readily susceptible to oxidation. The monounsaturated fatty acid esters, like oleic acid esters provide good low temperature properties and good oxidative stability. Recent developments in plant breeding and genetic engineering have made it possible to alter the fatty acid profiles of some vegetable oils. Due to their high oxidative stability many oils are enhanced with monounsaturated fatty acid, oleic acid content. Commercialized high oleic oils include high oleic sunflower oil, high oleic canola and high oleic soybean oil. The fatty acid esters derived from high oleic oils are particularly useful in lubrication applications owing to better oxidative stability and low temperature flow properties.

Fatty acid residues are a part of fatty acid or fatty acid ester consisting of long alkyl chain attached to a carbonyl carbon.

The fatty acid profile in terms of their saturated, mono- and polyunsaturated fatty acid composition of some vegetable oils and their oxidative stability as AOM hours (Active Oxygen Method, AOM, American Oil Chemists Society Official Method Cd 12-57) are shown in the table below.

TABLE 3

Fatty Acid Profile of Vegetable Oils

| Oil type | Saturated FA % | Monounsaturated FA % | Poly-unsaturated FA % | Oxidative Stability (AOM hrs) |
|---|---|---|---|---|
| Soybean | 16 | 22 | 62 | 15 |
| Canola | 7 | 56 | 37 | 17 |
| Palm | 50 | 39 | 11 | 50 |
| High Oleic Sunflower | 10 | 80 | 10 | 50 |
| High Oleic Canola | 7 | 75 | 18 | 44 |
| Jatropha | 21 | 47 | 32 | * |
| Sunflower | 15 | 20 | 65 | 15 |

*Not available

The polyol to which these fatty acids are esterified to also contributes to the low temperature fluidity.

In yet another embodiment $F^1A$ and $F^2A$ are both an 2-ethylhexanoic acid ester.

The mono or diester compounds of the present invention include

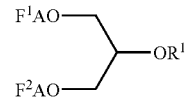

wherein $F^1A$ and $F^2A$ are each independently a fatty acid residue or a hydrogen atom, but not both hydrogen atoms, and $R^1$ is an alkyl group or alkylene ether containing ester.

Examples of alkyl groups are methyl, ethyl, or propyl groups. Examples of alkylene ether containing esters are of the formula where $R^1$ is

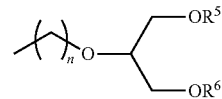

wherein, $R^1$ and $R^6$ are each independently a hydrogen, an alkyl, —C(=O)$R^{18}$ group or combinations thereof, provided when one or more $R^5$, $R^6$ is —C(=O)$R^{18}$, then each $R^{18}$ independently is an alkyl group.

and wherein n is 1 to 16, in particular n is 2 to 6.

B) Lubricants

The present invention is also directed to synthesis of model ester derivatives from symmetrical polyols for lubrication applications. The polyol esters made from polyols such as neopentyl glycol, trimethylol propane, pentaerythritol make excellent lubricants with good low temperature properties. The 2-alkyl glycerol esters also offer good low temperature properties.

There is a considerable interest in bio-based ester lubricants. (Kodali, Dharma R. "High Performance ester lubricants from natural oils." Industrial Lubrication and Tribology, 54,165-170, 2002), incorporated by reference in its entirety. The bio-based ester lubricants, derived from vegetable oils are considered to be environmentally benign due to ready biodegradability and low/no toxicity. Also their unique polar/non polar fatty acid ester structure provides inherent lubricity. Because of these reasons they are making inroads into lubricating fluids such as metal working fluids, hydraulic fluids, engine oils, fuels and fuel additives.

A lubricant forms a film on the surface of moving parts and reduces wear and friction. Lubricants contain a base fluid and additives as required for a given application. Lubricants require good low temperature flow properties, oxidative stability and lubricity.

Lubricants made with the symmetrical polyols of the present invention have functional similarity with the commercial polyols that are currently used in the lubricant industry such as 1,3-propanediol, neopentylglycol (NPG) or trimethylolpropane (TMP) that are derived from petroleum. The lubricants of the present invention have desirable low temperature fluid properties. The low temperature fluid properties of the compounds of the present invention are described in the synthesis section of the examples below.

Compounds 5-13, and 16 in the Examples Section below are useful as lubricants/lubricant additives as is or by further modification (e.g., transesterification with vegetable oils). Some of the compounds of the present invention and their thermal behavior are listed in Table 4 below.

TABLE 4

The DSC Thermal Behavior
(Melting and Crystallization Temperatures) of Compounds

| Compound # | Name | DSC Melting Temp. (Crystallization Temp.) |
|---|---|---|
| 5 | 2-Methyl glycerol* | No crystallization or melting up to −45° C. |
| 6 | 2-Ethyl glycerol* | No crystallization or melting up to −45° C. |
| 7 | 2-Propyl glycerol* | No crystallization or melting up to −45° C. |
| 8 | Palm olein fatty acid monoester of 2-methyl glycerol | 16° C. (11° C.) |
| 9 | Palm olein fatty acid monoester of 2-ethyl glycerol | 20° C. (14° C.) |
| 10 | Palm olein fatty acid monoester of 2-propyl glycerol | 12° C. (7° C.) |
| 11 | 2-Ethyl hexanoic acid ester of 2-methyl glycerol | No crystallization or melting up to −45° C. |
| 16 | 2-Ethyl hexanoic acid ester of Bis(1,3-dihydroxypropyl)-2,2'-n-hexyl ether | No crystallization or melting up to −45° C. |

*= 2-alkyl glycerols are also called as 2-alkoxy-1,3-propanediols.

A lubricant composition of the present invention includes a mono or diester including:

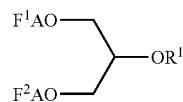

wherein $F^1A$, $F^2A$ and $R^1$ are as previously defined.

In another aspect, the lubricant composition includes at least one additive including viscosity-index improvers, pour point depressants, oxidation inhibitors, anti-wear agents, anti-foam additives, corrosion inhibitors, dispersants, detergents, acid neutralizers, rust inhibitors or combinations thereof.

In yet another aspect, a lubricant composition comprising the formula

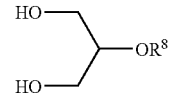

wherein $R^8$ is a methyl, ethyl, propyl, butyl, pentyl or hexyl group, and at least one additive comprising viscosity-index improvers, pour point depressants, oxidation inhibitors, anti-wear agents, anti-foam additives, corrosion inhibitors, dispersants, detergents, acid neutralizers, rust inhibitors or combinations thereof.

If the base fluid provides the required properties sufficiently for a given application, then the base fluid without any further formulation can be used as a lubricant. However most of the base fluids lack one or more properties for a given application that makes the base fluid to be formulated with various additives to enhance the deficient properties.

Typically, additives are present in amounts totaling from about 0.001% to about 20% based on weight. For example, a transmission fluid for diesel engines can be made that includes antioxidants, anti-foam additives, anti-wear additives, corrosion inhibitors, dispersants, detergents, and acid neutralizers, or combinations thereof. Hydraulic oil formulations can include antioxidants, anti-rust additives, anti-wear additives, pour point depressants, viscosity-index improvers and anti-foam additives or combinations thereof. Specific oil formulations will vary depending on the end use of the oil; suitability of a specific formulation for a particular use can be assessed using standard techniques. Further examples of ester formulations with various additives can be found in numerous patent and general literature including U.S. Pat. No. 6,465,401, entitled, "Oils with Heterogenous Chain Lengths" to Kodali et al. (2002), incorporated by reference in its entirety.

Additives including viscosity-index improvers, pour point depressants, oxidation inhibitors, antiwear agents, anti-foam additives, and corrosion inhibitors, dispersants, detergents, acid neutralizers, rust inhibitors or combinations thereof, can be added to the lubricant composition.

Typical antioxidants are aromatic amines, phenols, compounds containing sulfur or selenium, dithiophosphates, sulfurized polyalkenes, and tocopherols.

Rust inhibitors protect surfaces against rust and include alkylsuccinic type organic acids and derivatives thereof, alkylthioacetic acids and derivatives thereof, organic amines, organic phosphates, polyhydric alcohols, and sodium and calcium sulphonates.

Anti-wear additives adsorb on metal, and provide a film that reduces metal-to-metal contact. In general, anti-wear additives include zinc dialkyldithiophosphates, tricresyl phosphate, didodecyl phosphite, sulfurized sperm oil, sulfurized terpenes and zinc dialkyldithiocarbamate, and are used in amounts from about 0.05 to about 4.5 weight %.

Corrosion inhibitors include dithiophosphates and in particular, zinc dithiophosphates, metal sulfonates, fatty acids, acid phosphate esters and alkyl succinic acids.

Pour point depressants permit flow of the oil formulation below the pour point of the unmodified lubricant. Common pour point depressants include polymethacrylates, wax alkylated naphthalene polymers, wax alkylated phenol polymers and chlorinated polymers, and generally are present in amounts of about 1% or less.

Viscosity index can be increased by adding, for example, polyisobutylenes, polymethacrylates, polyacrylates, vinyl acetates, ethylene propylene copolymers, styrene isoprene copolymers, styrene butadiene copolymers and styrene maleic ester copolymers.

Anti-foam additives reduce or prevent the formation of a stable surface foam and are typically present in amounts from about 0.00003 to about 0.05 weight %. Polymethylsiloxanes, polymethacrylates, salts of alkylene dithiophosphates, amyl acrylate telomer and poly(2-ethylhexylacrylate-co-ethyl acrylate are non-limiting examples of anti-foam additives.

Detergents and dispersants are polar materials that serve a cleaning function. Detergents include metal sulfonates, metal salicylates and metal thiophosphonates. Dispersants include polyamine succinimides, hydroxy benzyl polyamines, polyamine succinamides, polyhydroxy succinic esters and polyamine amide imidazolines.

C) A Method to Prepare Serinol

Serinol (2-amino-1,3-propanediol) is a useful chemical as a radiocontrast agent or a pharmaceutical or chemical intermediate. A radiocontrast agent enhances an X-Ray image. Various synthetic methods exist to make this compound, however, the present invention provides a method of making serinol that is both easy and cost effective.

One method of making serinol is shown in Examples Section as synthesizing Compound 21 (serinol) which utilizes the synthesizing steps of making Compounds 1, 18 though 20 and finally Compound 21.

Generally, the method to prepare

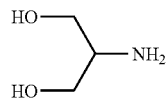

(compound I, serinol) of the present invention comprises the steps of
converting the hydroxyl of compound (II)

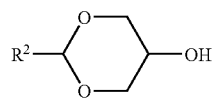

to a leaving group (L) to afford compound (III),

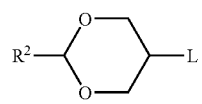

treating compound (III) under conditions wherein L is replaced by an azide to afford compound (IV)

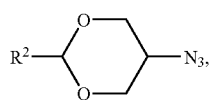

subjecting compound (IV) to a reducing agent to reduce the azide of compound (IV) to an amine compound (V)

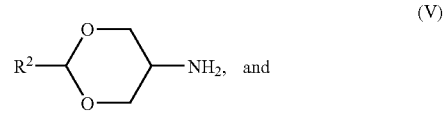

subjecting compound (V) to conditions suitable to afford compound (I), wherein $R^2$ is an alky or aryl group, and L is a leaving group. In particular, $R^2$ is a phenyl group.

Leaving groups are defined as any group that can be displaced from a carbon atom. Halide ions are good leaving groups as they are weak bases, whereas strong bases such as —OH are considered poor leaving groups. In particular the leaving group is a tosyl group.

A tosyl group (p-toluenesulfonate) is a highly reactive leaving group. Sulfonate groups ($RSO_2O$—) are also excellent leaving groups. Sulfonates in general are highly reactive leaving groups. Tosylate anions and sulfonate anions in general are resonance stabilized and are very weak bases.

A reducing agent is an element or compound that participates in an oxidation/reduction (redox) reaction to reduce another species. Complex metal hydrides are used as reducing agents, including for example, lithium aluminum hydride ($LiALH_4$), sodium hydride (NaH), lithium hydride (LiH), or sodium borohydride ($NaBH_4$). In particular, the reducing agent is $LiALH_4$.

In another embodiment the last step of the method of making serinol is under acidic conditions, in particular below about pH 6.

D) Tetrol Ether, Bis(1,3-Dihydroxypropyl)-2,2'-Alkylene Ether Compositions

The present invention is also directed to synthesis of tetrol compounds.

Synthesis of these compounds are outlined in the Examples Section below. Compound 15 utilizes the synthesizing steps of first making Compounds 1 and 14.

A compound having the formula:

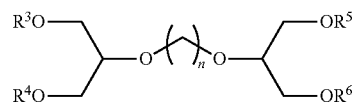

wherein $R^3$, $R^4$, $R^5$, $R^6$ are each independently a hydrogen, an alkyl, —C(=O)$R^{18}$ group or combinations thereof, provided when one or more $R^3$, $R^4$, $R^5$, $R^6$ is —C(=O)$R^{18}$, then each $R^{18}$ independently is an alkyl group; and wherein n is 1 to 16, in particular n is 2 to 6.

E) Tetrol Ether Ester, Esters of Bis(1,3-Dihydroxypropyl)-2,2'-Alkylene Ether Compositions The present invention is also directed to synthesis of tetrol ether ester compositions.

Synthesis of 2-ethyl hexanoic acid ester of tetrol ether, 2-ethyl hexanoic acid ester of bis(1,3-dihydroxy propyl)-2, 2'-n hexyl ether (Compound 16) is described in the Examples Section below.

In another embodiment the compounds have the formula:

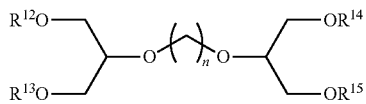

wherein $R^{12}$, $R^{13}$, $R^{14}$, $R^{15}$ are each independently a methacrylate, acrylate, vinyl ether or combinations thereof, and wherein n is 1 to 16, in particular n is 2 to 6.

In yet another embodiment $R^{12}$, $R^{13}$, $R^{14}$ or $R^{15}$ further comprises at least one alkyl containing group or —C(=O) $R^{18}$ group, wherein each $R^{18}$ independently is an alkyl group.

F) Polyesters

The present invention includes polyester compositions and methods of making polyesters and the methods of making crosslinked polyesters. Polyols are reacted with dicarboxylic acids to make polyesters.

Crosslinks are covalent bonds that link the adjacent polymer chains through the functional groups in the polymer chains. Polymerization of bifunctional monomers extend the polymer chain but do not crosslink as there are no functional groups left in the polymer chains. However, polymerization of polyfunctional (functionality>2) monomers can lead to crosslinking between the polymer chains.

Crosslinks are formed by heat, pressure, radiation or by mixing of unpolymerized or partially polymerized resin with various crosslinking agents. The crosslinking density depends upon the concentration of polyfunctionality and reactivity. The crosslinking density can be varied based upon the ratio of bifunctional to polyfunctional monomers. Crosslinking is a characteristic property of thermoset plastics that become hard upon cure. Crosslinked polymers are not soluble in organic solvents and it is difficult to measure their degree of polymerization or molecular weight. Crosslinking inhibits close packing of polymer chains and crystallinity. Also, it restricts molecular mobility and limits the extension of the polymer material under loading.

The most severe mechanism of decreasing molecular freedom is chemical crosslinking, which is linking the polymer chains together through covalent or ionic bonds to form a network. Occasionally, the term curing is used to denote crosslinking. There are a number of ways crosslinking can be brought about, but basically there are two categories: (1) crosslinking during polymerization by use of polyfunctional instead of difunctional monomers, and 2) crosslinking in a separate processing step after the linear (or branched) polymer is formed.

These linear polymers are not usually of a very high molecular weight and are generally referred as 'prepolymers'. The prepolymers possess either an unsaturation or a reactive functionality. When these prepolymers are reacted with low molecular weight or polymeric substances containing appropriate functional groups capable of reacting with reactive functional groups of the prepolymer, crosslinking takes place, resulting in a solid polymeric mass.

The low molecular weight or the polymeric material used to bring about the cure reaction is called the curing agent. The functionality of both the prepolymer and the curative plays an important role in determining whether the reaction between them will result in crosslinking or not. For crosslinking to take place, both the prepolymer and the curing agent should not only have a minimum functionality of two, but one or both of them should have functionality greater than two. Unless such molecules are present in the system, no crosslinking takes place but only the linear coupling of the prepolymer with curing agent molecules results. Linear coupling will result in another linear molecule of a longer chain length, i.e., higher molecular weight. The multifunctional (functionality>2) molecules provide sites where linear molecules can be connected through inter-chain links leading to crosslinking. The amount or degree of crosslinking i.e. crosslinking density, depends upon the ratio of the bifunctional to the multifunctional molecules present in the system.

2-alkylglycerols are very unique polyols having two functional groups, both being primary hydroxyls. The beta hydrogen present in glycerol is more labile making it susceptible to oxidation more readily compared to 2-alkylglycerols. 2-alkylglycerols are a unique class of polyols with excellent reactivity and the polymers derived from them will have unique properties. The use of 2-alkylglycerols as monomers in polyester applications and their advantages compared to glycerol and other commercial diols are illustrated below with 2-methylglycerol (2-methoxy-1,3-propanediol, MPDO) as an example.

2-Methoxy-1,3-propanediol (MPDO) is a substituted analogue of 1,3-propanediol, PDO, having primary hydroxyls on either end of the molecule. MPDO is derived from renewable raw material, glycerol. The secondary hydroxyl group in glycerol is converted to methyl ether leaving the primary hydroxyls intact. Because of this reason the reactivity of MPDO is comparable to other primary hydroxyl containing glycols and undergo condensation reactions at the same rate. This similarity in reactivity makes it suitable to substitute other diols like PDO, ethylene glycol or 1,4-butanediol to make co-polyesters. However, the 2-methoxy group present in MPDO influences the glycol segment conformation, flexibility and diffusivity in the melt. The steric bulk of the 2-methoxy group in the alkyleneoxy segment of the polyester affects the crystallization and other physical and functional properties. By varying the ratio of MPDO to the linear glycol in the polymerization process, the following advantages are realized.

The MPDO substituted polymers will have limited or no crystallinity due to methoxy group on the alkyleneoxy segment. These properties allow the resulting materials to be processed at lower temperatures, thus saving energy.

The copolymer will dissolve easily in various solvents compared to the homopolymer. The less overall crystallinity of the polymer makes it more suitable in certain applications like adhesives. The copolymer diol ratio controls the crystallization temperature and glass transition temperature. Additionally, the copolymer can be useful as plasticizer in other plastics to improve the flexibility of thermoplastics.

The advantages of 2-methoxy-1,3-propanediol (MPDO) compound in condensation polymerization of polyesters and polyurethanes may be differentiated in comparison to other analogous compounds such as glycerol, 1,3-propane diol, and 1,2-propane diol. Glycerol has two primary hydroxyl groups and one secondary hydroxyl group. It is difficult to produce linear polymers with the condensation reaction of glycerol with diacid because of the presence of two primary and one secondary hyrdoxyl functional groups. Instead, the condensation reaction produces branched and crosslinked polymers. The reactivity of primary hydroxyls differs considerably from secondary hydroxyl, the secondary being slow to react, albeit produces branched/crosslinked polymer.

The branched or crosslinked polymers will contain hydroxyl functionality that will render the polymer more hydrophilic and also prone to oxidation. The condensation reaction of 1,3-propane diol with diacid produces a crystalline polymer with limited solubility and normally requires elevated temperatures to process. On the other hand, the condensation reaction of 1,2-propane diol, a structural isomer to 1,3-propane diol, with diacid produces an amorphous and lower molecular weight polymer due to differential reactivity. Unlike 1,2-propanediol and 1,3-propane diol, MPDO based polyesters not only produce higher molecular weight materials but also are amorphous. This is attributed to hydroxyl groups of equal reactivity and the presence of flexible methoxy group.

These polymers are soluble in a wide range of solvents. These polymers are useful to prepare adhesives and coatings. The MPDO monomer is, therefore, useful to tune the crystallinity and processability of commercial polyesters such as polypropylene terephthalate (PPT) and polbutylene terephthalate (PBT) through copolymerization.

Furthermore, MPDO is useful to create elastic polyurethane polyesters. For example, hydroxyl terminated MPDO based polyesters can be reacted with diisocyanates using chain extenders such as 1,4-butane diol to prepare segmented thermoplastic polyurethane elastomer analogous to spandex fibers, for example, LYCRA® spandex fiber available from DuPont Company, Wilmington, Del.

The polymer structures of terephthalic acid polymerized with 1,3-propanediol (poly(propylene terephthalate), PPT) and its analogue 2-methoxypropanediol (poly(2-methoxypropylene terephthalate), PMPT) and a copolymer of 1,3-propanediol and 2-methoxy-1,3-propanediol (copolymer of PPT/PMPT) are shown below.

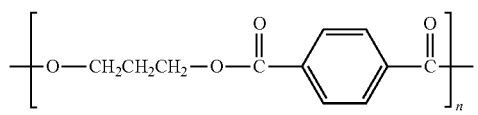

Polypropylene Terephthalate) PPT

AKA Poly(trimethylene Terephthalate) PTT

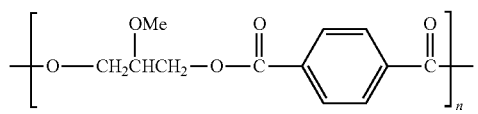

Poly(2-methoxypropylene Terephthalate) PMPT

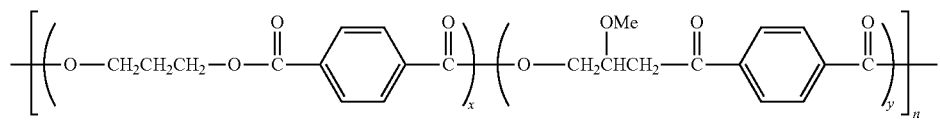

x and y are independently 1 or >1, ordered or random, segmented or block copolymer.

PPT/PMPT Copolymer

Thermoplastic polyesters based mainly on ethylene glycol and 1,4-butanediol have been extensively investigated during the last decades. The most well known members of this category of polymers are poly(ethylene terephthalate) (PET) and poly-(butylene terephthalate) (PBT).

PET is semicrystalline polyester possessing interesting thermal and mechanical properties, such as tensile strength and elongation at break, chemical resistance, high ability to form fibers, low permeability in $O_2$ and $CO_2$, and melt processability. Because of the excellent combination of the aforementioned properties, PET has found many applications in beverage and food packaging materials, fibers, electrical equipment, and even the automotive and construction industries.

PBT, the other important semicrystalline polyester, has higher crystallization rates than PET. For this reason and because of the excellent balance of properties and processing characteristics and especially faster and more economical molding characteristics and dimensional stability, it has found many applications in the preparation of mold articles alone or reinforced with glass fibers. It also exhibits high heat and chemical resistance, good electrical properties, and dielectric strength.

Poly(propylene terephthalate) (PPT), also known as Poly (trimethylene terephthlate) (PTT) is an engineering thermoplastic and many of its properties are between those of PET and PBT. PPT can be used in applications including films, mechanical parts, and mainly fibers. PPT is distinguished for its high elasticity, excellent recovery rate, very good dyeing in boiling water without carriers, strain resistance, high UV stability, low water absorption, and low electrostatic charging.

Poly(propylene terephthlate) (PPT) or poly(trimethylene terephthalate) (PTT) (which is manufactured by DuPont Company, Wilmington, Del. as SORONA® fibers; and by Shell Oil Company, Houston, Tex. as CORTERRA® polymer) is made by polycondensation of 1,3-propane diol (PDO) and either terephthalic acid or dimethyl terephthalate. This polymer has attracted the attention in the recent years after the development of production of 1,3-propane diol from starch derived glucose, a renewable resource.

Compounds 5-7 of the present invention can be substituted partially or fully for 1,3-propane diol (PDO) to obtain a polymer with altered physical properties (like lower Tg). Where PDO is used, 2-methoxy-1,3-propanediol (MPDO) can be used with slightly to markedly altered properties. For example, PDO is used in applications including films and fibers, adhesives, paints, powder coatings, inks, solvents, deicing agents, heat transfer fluids, coolants, as a monomer or even a chain extender.

PDO is also prepared from acrolein, or by hydroformylation of ethylene oxide. The PDO, prepared from acrolein, has carbonyl compounds as impurities, which adversely effect the color of the polymer. This problem was, however, addressed by using phenols or organophosphites in the polymerization. Production of PDO by fermentation of sugar, a renewable resource, is the most efficient process to date.

Polymers containing the longer section of aliphatic units are flexible and crystallize more rapidly. As a result, the melting point of the polymers decreases considerably on increasing the length of the aliphatic sequence between the aromatic rings in the chain.

Unlike PET and PBT, the PPT has odd number of methylene groups on the backbone, which requires more super cooling for crystallization.

2-Methoxy-1,3-propane diol (MPDO) monomer, a substituted analogue of PDO, is a symmetrical monomer with hydroxyl groups of equal reactivity. Further, MPDO is derived from renewable resource. Condensation of terephthalic acid with MPDO gave an amorphous polymer (MPPT). This polymer is soluble in wide range of common solvents, for example, chloroform, dichloromethane, tetrahydrofuran, methylethylketone or toluene. On the other hand, PPT is highly crystalline and is soluble only in selected solvents, such as phenols and substituted phenols.

The MPPT polymer provides improved processability due to methoxy pendant units. In other words, the methoxy pendant units inhibit the crystallization. These polymers will potentially find applications in powder coatings. Powder coating is applied as a free-flowing, dry powder. The coating is typically applied electrostatically and is then cured under heat. Powder coating is mainly used for coating metals of manufactured goods and auto parts. The powder coatings do not require any solvent and environmentally benign.

The amorphous nature of the polymer can be used to prepare curable thermoplastic elastomers. Further, incorporation of MPDO in PPT significantly modifies the physical properties of the polymer. The notable effect is decrease in glass transition temperature and crystallinity.

The possibility of tuning the crystallinity of these copolymers is adjusting the composition, which is an interesting approach towards designing new PPT materials with better balance between thermal, mechanical and optical properties.

The Examples Section below show the polymerization of polyesters of the present invention, polymer 1 to 5.

2-alkyl glycerols (can also be called as 2-alkoxy-1,3-propanediols) have the formula:

$$\text{HO} \diagdown \diagup \text{OR}^8$$
$$\text{HO} \diagup$$

wherein $R^8$ is an alkyl group. The alkyl group can be C1-C18, in particular, C2-C8.

MPDO and other 2-alkyl glycerols can be made into polyesters by condensing them with diacids.

In some embodiments, a polyester is the condensation product of one or more of a diacid, a diacid halide, or a diester and $$\text{HO} \diagdown \diagup \text{OR}^8$$
$$\text{HO} \diagup$$

wherein $R^8$ is an alkyl group.

In another embodiment, the diacid is $HOOC(CH_2)_n COOH$, wherein n is 0 to 20, in particular n is 2 to 8.

Examples of diacids include oxalic acid, malonic acid, succinic acid, glutaric acid, adipic acid, azelaic acid or sebacic acid, in particular adipic acid, azelaic acid or sebacic acid.

These polyesters have good low temperature fluid properties that can be used as lubricants. Lubricants of desired viscosities are synthesized, for example, by the condensation of 2-methoxy-1,3-propanediol with diacids such as adipic acid, azelaic acid or sebacic acid.

In one aspect, $R^8$ is a methyl, ethyl, propyl, butyl, pentyl or hexyl group.

In another aspect, the molecular weight of the polyester is greater than about 500 grams/mole, in particular between about 500 and about 100,000, and more particularly between about 1,000 to 80,000.

In yet another aspect, a terminal hydroxyl group of the polyester is derivatized with a methacrylate, an acrylate, a hydrolysable alkoxysilane, a photo initiator or combinations thereof.

In some embodiments, a crosslinked polyester is the condensation product of one or more of a diacid, a diacid halide, or a diester with a tetrol having the formula $$\text{HO} \diagdown \diagup \text{O} - (\diagup)_n - \text{O} \diagdown \diagup \text{OH}$$
$$\text{HO} \diagup \diagdown \text{OH}$$

wherein n is 1 to 16, in particular n is 2 to 6.

In some embodiments, a crosslinked polyester is a condensation product of one or more of a diacid, a diacid halide, or a diester, with a tetrol having the formula $$\text{HO} \diagdown \diagup \text{O} - (\diagup)_n - \text{O} \diagdown \diagup \text{OH}$$
$$\text{HO} \diagup \diagdown \text{OH}$$

wherein n is 1 to 16, in particular n is 2 to 6, and a diol.

Optionally, diols can be added to the polyester composition to control the cross-linking density. Diols include 1,3-propane diol, butane diol. The average functionality of the reactants determines the crosslinking density. For example, linear polymers are produced when the reactants possess the difunctional moiety. If the average functionality is >2, crosslinked polymers are produced. So, the higher the functionality of the reactants the greater the frequency of crosslinks, hence the higher crosslinking density.

The invention further includes methods of making polyesters and curable polyesters described herein.

Polyesters are condensation polymers that contain ester functionality in the polymer chain. The polyesters can be synthesized by number of methods such as, azeotropic esterification, where alcohol is condensed with diacid (or functional equivalent, e.g., diester) with the removal of water (or alcohol); ring opening polymerization where aliphatic lactones prepared under mild conditions are polymerized anionic or cationic conditions; transesterification where the ester and alcohol terminated oligomers are condensed to form a polymer; acylation where a acid chloride is condensed with polyol to form a polymer with the elimination of hydrogen chloride. Polyesters can be prepared with any of the glycerol derivatives described herein.

G) Polyurethanes

The present invention pertains to polyurethane compositions and methods of making polyurethane compositions. Additionally, reacting the symmetrical polyols of the present invention with isocyanates produce flexible and rigid polyurethane foams.

Compared to glycerol, 2-methoxy-1,3-propane diol, MPDO, offers a number of advantages in the synthesis of polyurethanes. The reaction of glycerol with diisocyanate invariably produces crosslinked polyurethanes. Whereas, the reaction of MPDO with diisocyanate produces linear, functional polyurethanes of predetermined molecular weight that can be further modified.

Polyurethanes are produced by reacting aromatic or aliphatic diisocyanate with a polyol. Polyurethane properties and performance such as densities and hardnesses can be modified by varying the type of monomer used and adding other substances.

Polyurethanes are among the most widely used and versatile of all polymers, ranging from soft elastomers, adhesives and foams, to hard plastics. They are manufactured from many different starting materials and a broad range of additives.

Polyurethanes are produced by the step-growth addition reaction of a polyisocyanate with a polyalcohol (polyol) in the presence of a catalyst and other additives. The main reaction product of a polyurethane is a urethane linkage, —RNH-COOR'— formed by reacting an isocyanate group, —N═C═O with a hydroxyl group, —OH. A polyisocyanate is a molecule with two or more isocyanate functional groups, R—(N═C═O)$_{n\geq2}$ and a polyol is a molecule with two or more hydroxyl functional groups, R'—(OH)$_{n\geq2}$. In polyurethane synthesis, by controlling variables such as functionality, chemical composition and the molecular structure and weight of the different reactants, a wide class of materials with significantly different properties can be produced. The properties of the polyurethane are determined mainly by the choice of polyol. The diisocyanate exerts some influence on properties, and must be suited to the application.

Generally, polyurethane production is based on low-molecular weight aliphatic hydroxyl-terminated polyethers such as poly(propylene glycol) or polyesters such as poly(diethylene glycol adipate). Low molecular weight diols such as 1,4-butane diol and 1,6-hexane diol are used as chain extenders. The most important isocyanates are a mixture of 2,4-toluenediisocyanate (TDI), methylene-4,4'-diphenyldiisocyanate (MDI). Aliphatic isocyanate such as 1,6-hexamethylene diisocyante is used primarily to make light stable coatings. The nature and the functionality of reactants control the reactivity and crosslinking density. Polyurethane can be made in a variety of densities and hardnesses by varying the type of monomers used and adding other substances to modify their characteristics, notably density, or enhance their performance. Other additives can be used to improve the fire performance, stability and chemical resistance properties of the polyurethane products.

Softer and more flexible polyurethanes result when linear difunctional polyethylene glycol segments are used. The flexible polyurethanes find use in foams, elastomers, coatings, sealants and adhesives. More rigid products result if polyfunctional polyols are used, as these create a three-dimensional crosslinked structure which can be in the form of a low-density foam. An even more rigid foam can be made with the use of specialty trimerization catalysts which create cyclic structures within the foam matrix, giving a harder, more thermally stable structure, designated as polyisocyanurate foams. Such properties are desired in rigid foam products used in the construction sector.

Polyurethane foam (including foam rubber) is usually made by adding small amounts of volatile materials, called blowing agents, to the reaction mixture. The volatile chemicals such as acetone or methylene chloride, or fluorocarbons act as good blowing agents. Another common route to produce foams is the addition of water to one of the liquid precursors of polyurethane before they are mixed together. This reacts with a portion of the isocyanate, generating carbon dioxide throughout the liquid, creating relatively uniform bubbles which then harden to form a solid foam as polymerization progresses. In a typical production, the isocyanate, polyol, water and other ingredients are rapidly and intensively mixed and immediately poured to carry out the foaming.

Applications of polyurethanes are numerous. Comfortable, durable mattresses and automotive and domestic seating are manufactured from flexible foam. Rigid polyurethane foam is one of the most effective, practical, thermal insulation materials, used in applications ranging from domestic refrigerators to large industrial buildings. Polyurethane adhesives are used to make a wide variety of composite wood products from load-bearing roof beams to decorative cladding panels. Products ranging from shoe soles, sports equipment, car bumpers and 'soft front ends' are produced from different forms of polyurethane elastomers. Many of us are clothed in fabrics containing polyurethane fibers or high performance breathable polyurethane membranes. Highly demanding medical applications use biocompatible polyurethanes for artificial joints and implant coatings. In such applications, polyurethanes made from bio-based polyols will broaden the scope and functionality. Polyurethane coatings protect floors and bridges from damage/corrosion. Adhesives are used in the construction of items as small as an electronic circuit board and as large as an aircraft. Advanced glass and carbon fiber reinforced composites are being evaluated in the automotive and aerospace industries.

Polyols containing primary hydroxyl groups are a lot more reactive than secondary or tertiary hydroxyl containing compounds. Compounds 5-7, 15, 21, 24 and 26, in the Examples Section below, are useful as chain extenders and crosslinking agents in polyurethanes, paints, sealants, adhesives etc. Polyether polyols such as Polymer 9b are used to make polyurethanes that are widely used as hotmelt adhesives.

Similarly, reacting the symmetrical polyols with isocyanates produce flexible and rigid polyurethane foams.

In some embodiments polyurethanes of the present invention are the condensation product of a diisocyanate and

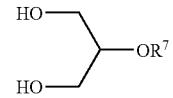

wherein $R^7$ is an alkyl, substituted alkyl, aryl or substituted aryl group.

Diisocyanates useful for the present invention include, for example, toluene diisocyanate (TDI), isophorone diisocyanate (IPDI); methylene diphenylene diisocyanate (MDI), or hexamethylene diisocyanate (HDI).

In particular, $R^7$ is methyl, ethyl, propyl, butyl, pentyl or hexyl group.

The molecular weight of the polyurethane is greater than about 500 grams/mole, in particular between about 500 and about 150,000, and more particularly between about 1,000 to 100,000.

The hydroxyl group of the polyurethane is derivatized with a methacrylate, an acrylate or a vinyl ether or hydrolysable alkoxysilanes or a photoinitiator.

Hydrolysable alkoxysilanes are mono, di or trialkoxy silanes. The alkoxy groups are in particular C1-C4.

A photoinitiator, upon absorption of light, undergoes a photoreaction, producing reactive species that are capable of initiating the polymerization of the polymerizable constituents. General examples of photoinitiators include benzophenone, anthraquinone, benzoin and others. Commercial photoinitiators, for example, IRGACURE® 2959, IRGACURE® 184, IRGACURE® 819, or IRGACURE® 1173 are available from Ciba Specialty Chemicals Corporation, Tarrytown, N.Y.

A crosslinked polyurethane is a thermoset and cannot be dissolved in solvents.

In one embodiment a crosslinked polyurethane of the present invention is the condensation product of a diisocyanate and a tetrol having the formula

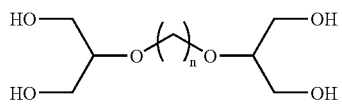

wherein n is 1 to 16, in particular n is 2 to 6.

The present invention also includes a crosslinked polyurethane which is a condensation product of diisocyanate and a tetrol having the formula

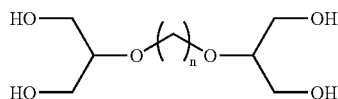

wherein n is 1 to 16, in particular n is 2 to 6, and a diol.

Optionally, diols can be added to the polyurethane composition to control the cross-linking density. Diols include 1,3-propane diol, butane diol. The average functionality of the reactants determines the crosslinking density. For example, linear polymers are produced when the reactants possess the difunctional moiety. If the average functionality is >2, crosslinked polymers are produced. So, the higher the functionality of the reactants the greater the frequency of crosslinks, hence the higher crosslinking density.

The invention further includes methods of making polyurethanes described herein.

Polyurethanes are produced by reacting diisocyanate containing compound (like MDI or TDI) and a polyol in the presence of a catalyst. For example 1,3-propane diol reacts with MDI to give a structure —[O—CO—NH—$(CH_2)_6$—NH—CO—O—$(CH_2)_3$—]$_n$—. Polyurethanes can be prepared with any of the glycerol derivatives containing hydroxyl groups described herein.

H) Triazole and Tetrazole Compounds

The present invention provides for triazole and tetrazole compounds.

Condensation of azides with triple bond containing acetylene or nitrile forms triazole or tetrazole containing compounds respectively. This reaction has been discovered recently and called "click" chemistry. This reaction has wide applications in synthesizing triazole and tetrazole derivatives that have applications in agrochemicals, corrosion inhibitors, dyes, optical brighteners and pharmaceuticals.

Click chemistry is a newer synthetic approach to make triazole and tetrazole molecules that can accelerate the bioactive molecule discovery process. These reactions are reliable and are insensitive to oxygen and water. (reference: Kolb H. C. and Sharpless K. B. *Drug Discovery Today*, 2003, 8, 1128.)

Generally, 1,5-disubstituted tetrazoles are produced when the substituted azides are condensed with substituted nitriles. Recently Kantam M. L. et al., Nanocrystalline ZnO as an Efficient Heterogeneous Catalyst for the Synthesis of 5-substituted 1H-Tetrazoles, Adv. Synth. Catal. 347, 1212-1214, 2005 described the use of zinc oxide as a catalyst to produce tetrazoles. For example condensation of 1,3-benzylideneglycerol-2-azide with alkyl or aryl substituted nitrile will produce the corresponding 5-alkyl or aryl tetrazole.

The condensation of substituted azide with alkyne at elevated temperature gives both 1,4- and 1,5-disubstituted triazoles with poor regioselectivity. However, triazoles with excellent regioselectivity can be synthesized by using a Cu (I) catalyst obtaining 1,4-isomer as a predominant product.

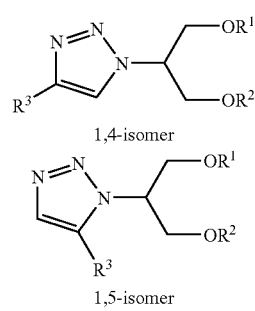

1,4-isomer 1,5-isomer

For the preparation of triazole derivates click chemistry was used by condensing 1,3-benzylidenepropane-2-azide with phenyl acetylene using cuprous iodide and toluene at reflux temperature. Preparation of triazole compounds are below in the Examples Section.

The possible isomers for this reaction are:

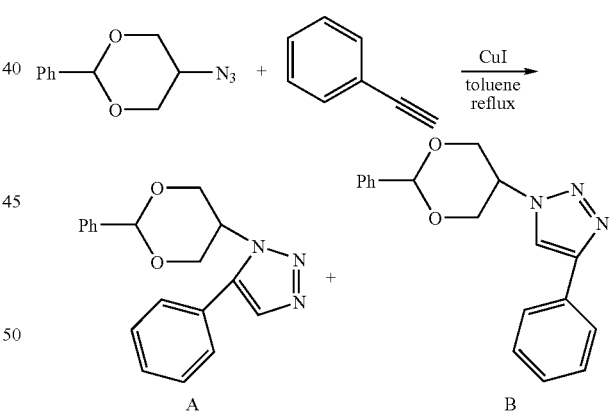

The major product of the reaction under the catalytic conditions is 1,4-substituted triazole, structure B above.

The present invention provides a compound including the formula:

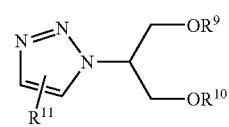

wherein $R^9$ and $R^{10}$ are each independently a hydrogen, an alkyl group or an aryl group, and $R^{11}$ is an alkyl group, an aryl group or combinations thereof.

I) Pendant Polyol Acrylate or Polyol Vinylether Polymers

The pendant dihydroxyglycerol containing polymers (oligomers) were synthesized from 1,3-benzylideneglycerol. In one example 1,3-benzyledeneglycerol is esterified with acrylic acid. The acrylate derivative is polymerized and deketalized to obtain an oligomer/polymer containing pendant 1,3-dihydroxyglycerol derivatives.

Similarly, 1,3-benzylideneglycerol is condensed with chloroethylvinyl ether to obtain an ether derivative. The polymerized vinyl ether is deprotected to give a pendent 1,3-dihydroxyglycerol ethylether.

The above polymers are useful in number of applications, for example, as hydrogels, crosslinking agents, or polyol substitutes.

The synthetic procedures adopted to synthesize the monomers are shown in the Examples Section below as synthesis of Compounds 23, 24, 25, 26 and synthesis of Polymers 8a, 8b, 9a and 9b.

In another embodiment a compound including the formula:

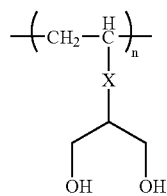

wherein n is greater than 10, in particular n is 10 to 100,000, more particularly, n is 20 to 50,000 and wherein X is —O—, —O—CH$_2$CH$_2$—O—, —CONH— or —COO—.

For example, if acrylic acid or an acrylic ester is reacted with 2-aminoglycerol (serinol), then X in the formula above would become —CONH—.

J) Fuel Compositions

Gasoline and diesel fuels are refined petroleum products which are burned in internal combustion engine to produce power used for work, transportation and energy. Gasoline is a petroleum-derived liquid mixture consisting primarily of hydrocarbons and enhanced with benzene or iso-octane to increase octane ratings, used as fuel in internal combustion engines. Diesel or diesel fuel is a specific fractional distillate of fuel oil (mostly petroleum) that is used as fuel in a diesel engine. On the other hand, biodiesel refers to alkyl esters of fatty acids, a diesel-equivalent, processed fuel derived from fats and oils.

Fuel additives improve the burning characteristics of the fuel to provide greater efficiency, power and less polluting emissions. Many fuel additives include oxygenates, corrosion inhibitors, antioxidants and lubricants. The fuel additives reduce exhaust emissions, such as particulates, nitrogen oxides and carbon monoxide. Some of the fuel additives include alkyl carbonates, methyl tertiary butyl ether and ethanol. Currently methyl tertiary butyl ether is being replaced by bio-based ethanol.

U.S. Pat. No. 5,308,365 to Kesling Jr. et al., incorporated by reference in its entirety, describes a diesel fuel additive containing a dialkyl and a trialkyl derivative of glycerol to reduce particle emissions. U.S. Pat. No. 5,578,090 to Bradin, incorporated by reference in its entirety, describes a fuel additive composition including fatty acid alkyl esters and glycerol ethers. U.S. Pat. No. 6,890,364 to Delfort et al., incorporated by reference in its entirety, describes diesel fuel compounds including glycerol acetals. U.S. Pat. No. 3,032,971 to Shotton, incorporated by reference in its entirety, describes glycol ethers as anti-icing additives to fuels. Petroleum and Coal, 45, 54-57, 2003, incorporated by reference in its entirety, describes etherification of glycerol with tertiary butanol and use in fuel as oxygenates.

Compounds 5-13, and 17 in the Examples Section below can be used as biorenewable fuel additives and as oxygenates.

The present invention is also directed to a fuel composition including gasoline, diesel fuel or biodiesel used in internal combustion engine and at least one glycerol ether including the formula:

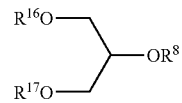

wherein $R^{16}$ and $R^{17}$ are each independently a hydrogen or —C(=O)$R^{18}$ group, provided when one or more $R^{16}$, $R^{17}$ is —C(=O)$R^{18}$, then each $R^{18}$ independently is an alkyl group; group and $R^8$ is an alkyl group.

In another embodiment, $R^8$ is an alkyl group and $R^{16}$ and $R^{17}$ are hydrogen.

In some embodiments, $R^{16}$, $R^{17}$ and $R^8$ are each independently an alkyl group.

In one aspect, the diesel fuel is from petroleum.

In another aspect the biodiesel is a mixture of fatty acid alkyl esters from fats and oils. Fats and oils are substances composed of triacylglycerols, derived from plants and animals. Nominally, oils are liquid at room temperature, and fats are solid.

EXAMPLES

Thin layer chromatography (TLC) analysis was performed on a Merck 60 F254 silicagel coated aluminum sheets with appropriate solvent system and visualization as described in the Examples Section.

Melting points were determined on a DBK programmed melting point apparatus.

Infra Red (IR) spectra were recorded on a Perkin Elmer instrument in the region 4000-370 cm-1 as KBr pellets or neat.

Nuclear magnetic resonance (NMR) was performed on a 1H NMR. Spectra were recorded using either a Varian Gemini 200 (200 MHz) spectrophotometer or a Bruker DRX 500-MHz NMR spectrometer in CDCl3 and tetramethylsilane (TMS) as internal standard.

Differential scanning calorimetry (DSC) was measured by a TA Instruments 2920 Differential Scanning Calorimeter. For polymers, each sample was subjected to several heating/cooling cycles to obtain reproducible data. For the individual compounds thermal history and the heating and cooling rates are varied and are given as described below.

Inherent viscosity (IV) is defined in "Preparative Methods of Polymer Chemistry", W. R. Sorenson and T. W. Campbell, 1968 (second ed.), p. 49. It is determined at a concentration of 0.5 g/100 ml of a o-chloro phenol solvent at ambient temperature.

A) Synthesis of 1,3-benzylidine glycerol (Compound 1)

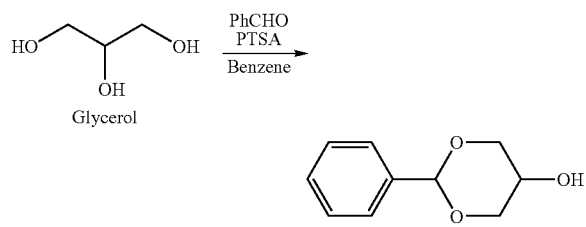

To a stirred solution of glycerol (100 g, 1.086 mol) in dry benzene (1 L), benzaldehyde (115 g, 1.086 mol) was added at room temperature followed by catalytic addition of para-toluene sulfonic acid (PTSA) (1.8 g, 0.01 mol) and Dean Stark apparatus (a piece of laboratory glassware used in synthetic chemistry to collect water from a reactor—a distilling trap) was fixed. Reaction mass was stirred at reflux for 6 h. Formation of water indicated the progress of reaction. After completion of the reaction, benzene was removed in vacuum. Crude reaction mass was slowly dissolved in 1:1 mixture of hexane and benzene (4 L) while stirring and kept in deep freeze for 24 h. Formed white solid was filtered and filtrate was kept in deep freeze. White solid was once again dissolved in 1:1 mixture of hexane and benzene (2 L) and kept in deep freeze. Formed solid was filtered. This process was repeated until the filtrate does not form any solid and finally got Compound 1 (75 g, 38%) as a white fluffy crystalline solid. M. Pt. (DSC) 84° C. (Ref. 83.5° C.); Infrared (IR) spectroscopy (neat): 1013, 1087, 1155, 1650, 2851, 3285 cm$^{-1}$; $^1$H Nuclear magnetic resonance (NMR) spectroscopy (200 M Hz, CDCl$_3$) δ3.0 (s, 1H), 3.5 (s, 1H), 4.0-4.3 (dd, 4H, J=6.2 Hz), 5.5 (s, 1H), 7.0-7.3 (m, 5H).

Thin Layer Chromatography (TLC) Analysis: 3:7 EtOAc:Hexane R$_f$ 0.3, UV active and α-naphthol charring.

Note: For Compound 1, the differential scanning calorimetry (DSC) melting temperatures are determined by loading the solid sample at room temperature and heating to a temperature 20° C. above the melting temperature of the compound at 5° C./minute. The melting temperature of the compound is taken as the temperature where most of the compound (>90% of the area under the melting curve) is melted into liquid.

B. Synthesis of 2-Methyl 1,3-benzylidine Glycerol (Compound 2)

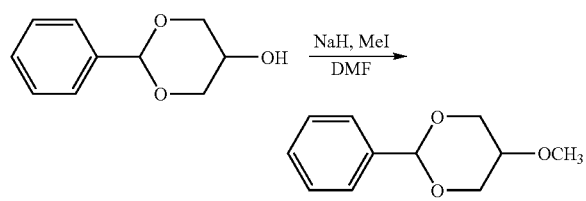

To a stirred solution of alcohol of Compound 1 (20 g, 0.11 mmol) in dry N,N-Dimethylformamide (DMF) (200 mL) sodium hydride (5.28 g., 0.22 mol, 60% w/w in paraffin oil) was added at 0° C. After 30 min methyl iodide (9.2 mL, 0.165 mol) was added followed by tetrabutyl ammonium bromide (TBABr) (0.5 g) at 0° C., reaction mixture was warmed to room temperature and stirred for 12 h. It was quenched with saturated aq. NH$_4$Cl solution (200 mL) at 0° C. and extracted with ethyl acetate (2×250 mL). The combined organic layers were washed with water (200 mL), brine (100 mL), dried sodium sulfate (Na$_2$SO$_4$), concentrated to afford Compound 2 (21 g., quantitative) as a pale yellow solid with a melting temperature (DSC) of 55° C. Infrared (IR) spectroscopy (neat): 1012, 1086, 1147, 1396, 1452, 2827, 2866, 2929, 2978 cm$^{-1}$; $^1$H Nuclear magnetic resonance (NMR) spectroscopy (200 M Hz, CDCl$_3$) δ3.1 (s, 1H), 3.5 (s, 3H), 4.0 (d, 4H, J=7.1 Hz), 4.3 (d, 2H, J=7.1 Hz), 5.5 (s, 1H), 7.3-7.5 (m, 5H).

TLC Analysis: 1:1 EtOAc:Hexane R$_f$ 0.6, UV active and α-naphthol charring.

Note: For Compound 2, the DSC melting temperatures are determined by loading the solid sample at room temperature and heating to a temperature 20° C. above the melting temperature of the compound at 5° C./minute. The melting temperature of the compound is taken as the temperature where most of the compound (>90% of the area under the melting curve) is melted into liquid.

C. Synthesis of 2-Ethyl 1,3-benzylidine Glycerol (Compound 3)

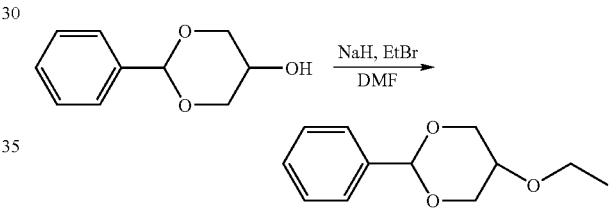

Compound 1 (20 g., 0.11 mole) is condensed with ethyl bromide by adopting a similar procedure followed for the preparation of Compound 2. The reaction workup gave Compound 3 as a pale yellow liquid (23 g., quantitative). IR (neat): 1093, 1388, 1673, 1734, 2860, 2974 cm$^{-1}$; $^1$H NMR (200 M Hz, CDCl$_3$) δ1.3 (t, 3H, J=6.2 Hz), 3.3 (m, 1H), 3.6-3.8 (m, 2H), 4.0-4.4 (dd, 4H, J=6.2 Hz), 5.5 (s, 1H), 7.3-7.6 (m, 5H). TLC Analysis: 1:1 EtOAc:Hexane R$_f$ 0.6, UV active and α-naphthol charring.

D. Synthesis of 2-Propyl 1,3-benzylidine Glycerol (Compound 4)

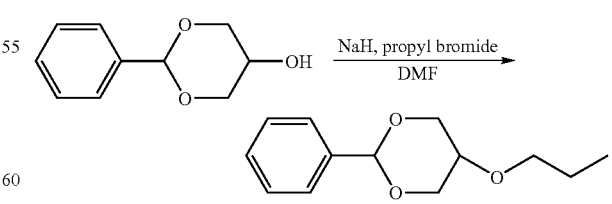

Compound 1 (20 g., 0.11 mole) is condensed with propyl bromide by adopting a similar procedure followed for the preparation of Compound 2. The reaction workup gave Compound 4 as a less viscous pale yellow liquid (24 g., quantitative). $^1$H NMR (200 M Hz, CDCl$_3$) δ0.9 (t, 3H, J=6.6 Hz), 1.7

(m, 2H), 3.2 (m, 1H), 3.5 (t, 2H, J=6.6 Hz), 4.0-4.5 (dd, 4H, J=6.6 Hz), 5.5 (s, 1H), 7.3-7.5 (m, 5H). TLC Analysis: 1:1 EtOAc:Hexane $R_f$ 0.6, UV active and α-naphthol charring.

E. Synthesis of 2-Methyl Glycerol; Also Called as 2-Methoxy-1,3-Propane Diol, MPDO (Compound 5)

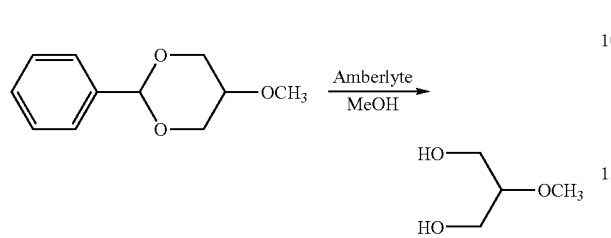

To a stirred solution of Compound 2 (22 g., 0.113 mol) in methanol (150 mL) amberlyte resin (2.2 g.) was added and stirred at room temperature for 12 h. The reaction mixture was filtered and organic layer was concentrated and the residue purified through column chromatography (60-120 Silica gel, 1:2 EtOAc-Hexane) to give diol from Compound 5 (10 g, yield: 83%) as a yellow liquid IR (neat): 755, 1068, 1214, 1462, 1663, 2927, 3380 cm$^{-1}$ $^1$H. NMR (200 M Hz, CDCl$_3$) δ3.5 (s, 3H), 3.6-3.8 (m, 5H), 4.8 (br.s, 2H). TLC Analysis: 1:1 EtOAc:Hexane $R_f$ 0.1, α-naphthol charring.

DSC thermal behavior: No crystallization or melting was observed when cooled to −45° C. and heated to room temperature.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C. minute from −45° C. to 25° C.

F. Synthesis of 2-Ethyl Glycerol (Compound 6)

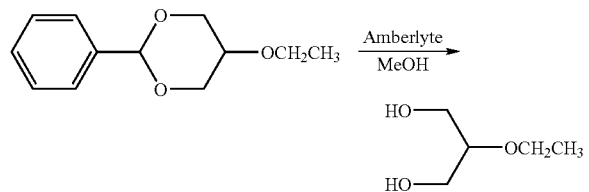

Treatment of Compound 3 (23 g., 0.11 mole) to a similar procedure followed for Compound 5, gave diol of Compound 6 as a free flowing yellow liquid (11 g, yield: 81%). IR (neat): 757, 1055, 1215, 1667, 2881, 3012, 3387 cm$^{-1}$ $^1$H. NMR (200 M Hz, CDCl$_3$) δ1.2 (t, 3H, J=8.6 Hz), 3.2-3.4 (m, 2H), 3.6-3.8 (m, 5H). TLC Analysis: 1:1 EtOAc:Hexane $R_f$ 0.1, α-naphthol charring.

DSC thermal behavior: No crystallization or melting was observed when cooled to −45° C. and heated to room temperature.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C. minute from −45° C. to 25° C.

G. Synthesis of 2-Propyl Glycerol (Compound 7)

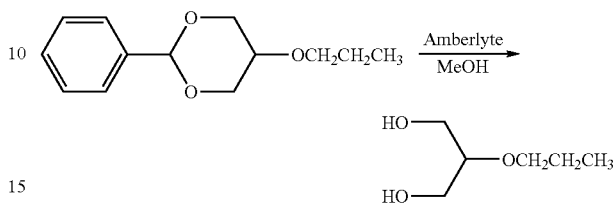

The treatment of Compound 4 (25 g., 0.113 mole) similar to the procedure followed for Compound 5, gave diol of Compound 7 as a free flowing yellow liquid (10 g, yield: 66%). $^1$H NMR (200 M Hz, CDCl$_3$) δ0.9 (t, 3H, J=8 Hz), 1.6-1.8 (m, 2H, H-3), 2.5 (br.s, 2H), 3.4-3.8 (m, 7H). TLC Analysis: 1:1 EtOAc:Hexane $R_f$ 0.1, α-naphthol charring.

DSC thermal behavior: No crystallization or melting was observed when cooled to −45° C. and heated to room temperature.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C. minute from −45° C. to 25° C.

H. Synthesis of Palm Olein Fatty Acid Mono-Ester of 2-methyl Glycerol (Compound 8)

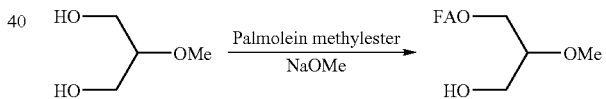

To a stirred solution of NaOMe (0.2 g., 0.004 mol) in dry toluene (15 mL) the diol of Compound 5 (1 g., 0.008 mol) was added at room temperature under nitrogen atmosphere. After 10 min palm olein methyl ester (2.38 g., 0.008 mol) was added followed and stirred for 12 h. It was quenched with saturated aq. NH$_4$Cl solution (20 mL) at 0° C. and extracted with ethyl acetate (2×25 mL). The combined organic layers were washed with water (20 mL), brine (10 mL), dried (Na$_2$SO$_4$), concentrated to afford crude Compound 8 (0.8 g., 14%) as a pale yellow liquid. $^1$H NMR (200 M Hz, CDCl$_3$) δ0.8-0.9 (m) 1.2-1.4 (m), 1.5-1.7 (m), 1.9-2.1 (m), 2.3 (t, J=6.6 Hz), 3.4-3.7 (m), 4.16 (d, J=5.8 Hz), 5.25-5.35 (m). TLC Analysis: 1:1 EtOAc:Hexane $R_f$ 0.4, UV active and α-naphthol charring.

The DSC thermal behavior showed that this compound upon cooling crystallized at 11° C. and upon heating melted at 16° C. (Adopted DSC procedure below)

DSC procedure: A pre-weighed sample in DSC pan is loaded at 25° C. Cooled at 2.5° C./minute to −45° C. The sample is held isothermally at −45° C. for 10 minutes. Then it is heated at 5° C./minute to 50° C.

I. Synthesis of Palm Olein Fatty Acid Mono-Ester of 2-ethyl Glycerol (Compound 9)

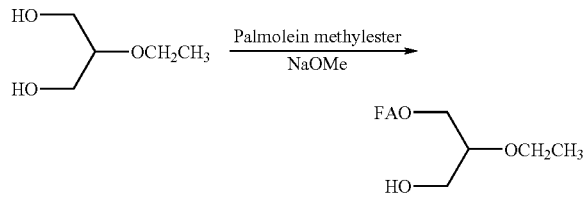

The same procedure was followed, which is for the preparation of Compound 8 to give Compound 9 as a pale yellow liquid. $^1$H NMR (200 M Hz, CDCl$_3$) δ0.82-0.9 (m) 1.2-1.4 (m), 1.55-1.7 (m), 1.92-2.1 (m), 2.3 (t, J=6.6 Hz), 3.5-3.7 (m), 4.16 (d, J=4.8 Hz), 5.25-5.35 (m). TLC Analysis: 1:1 EtOAc:Hexane R$_f$ 0.4, UV active and α-naphthol charring.

The DSC thermal behavior showed that this compound upon cooling crystallized at 14° C. and upon heating melted at 20° C. (Adopted DSC procedure below).

DSC procedure: A pre-weighed sample in DSC pan is loaded at 25° C. Cooled at 2.5° C./minute to −45° C. The sample is held isothermally at −45° C. for 10 minutes. Then it is heated at 5° C./minute to 50° C.

J. Synthesis of Palm Olein Mono-Ester of 2-propyl Glycerol (Compound 10)

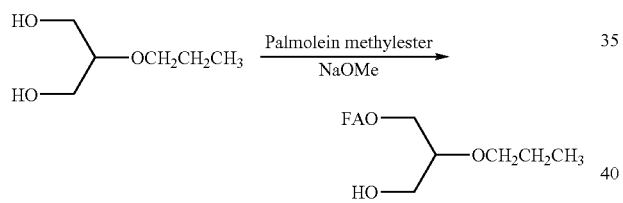

The same procedure was followed, which is for the preparation of Compound 8 to give crude Compound 10 (1 g., 10%) as a pale yellow liquid. $^1$H NMR (200 M Hz, CDCl$_3$) δ0.82-0.98 (m) 1.2-1.4 (m), 1.5-1.7 (m), 1.9-2.1 (m), 2.3 (t, J=6.6 Hz), 3.4-3.7 (m), 4.18 (d, J=5.8 Hz), 5.25-5.38 (m). TLC Analysis: 1:1 EtOAc:Hexane R$_f$ 0.4, UV active and α-naphthol charring.

The DSC thermal behavior showed that this compound upon cooling crystallized at 7° C. and upon heating melted at 12° C. (Adopted DSC procedure below)

DSC procedure: A pre-weighed sample in DSC pan is loaded at 25° C. Cooled at 2.5° C./minute to −45° C. The sample is held isothermally at −45° C. for 10 minutes. Then it is heated at 5° C./minute to 50° C.

K. Synthesis of 2-Ethyl Hexanoic Acid Ester of 2-methyl Glycerol (Compound 11)

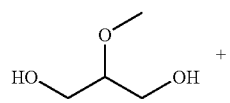

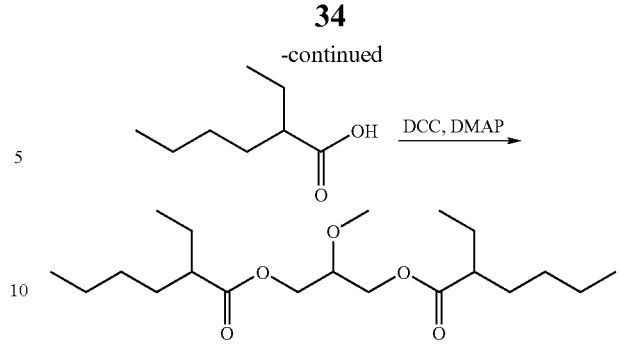

To a stirred solution of 2-ethyl hexanoic acid (13.58 g., 0.094 mol) in dry dichloromethane (50 mL), 1,3-dicyclohexylcarbodiimide (DCC) (19.43 g., 0.094 mol), followed by the diol of Compound 5 (5 g., 0.047 mol) and dimethylaminopyridine (DMAP) (11.5 g., 0.094 mol) were added at 0° C. and stirred for 24 h at room temperature. Reaction mass was filtered and filtrate was washed with sodium bicarbonate (NaHCO$_3$) solution and water. Organic layers were washed with brine (10 mL), dried (Na$_2$SO$_4$) and concentrated. The crude residue was purified by column chromatography (60-120 Silica gel, 1:20 EtOAc:Hexane) to afford Compound 11 (8.2 g., 49%) as a light yellow liquid. IR (neat): 1214, 1416, 1729, 2937, 3020 cm$^{-1}$; $^1$H NMR (200 M Hz, CDCl$_3$): δ0.9 (m, 12H), 1.2-1.8 (m, 16H), 2.2-2.4 (m, 2H), 3.4 (s, 3H), 3.5 (m, 1H), 4.0-4.3 (m, 4H). TLC Analysis: 1:9 EtOAc:Hexane R$_f$ 0.7, UV active and α-naphthol charring.

DSC behavior: No crystallization or melting was observed when cooled to −45° C. and heated to room temperature.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C. minute from −45° C. to 25° C.

L. Synthesis of 2-Ethyl Hexanoic Acid Ester of 2-ethyl Glycerol (Compound 12)

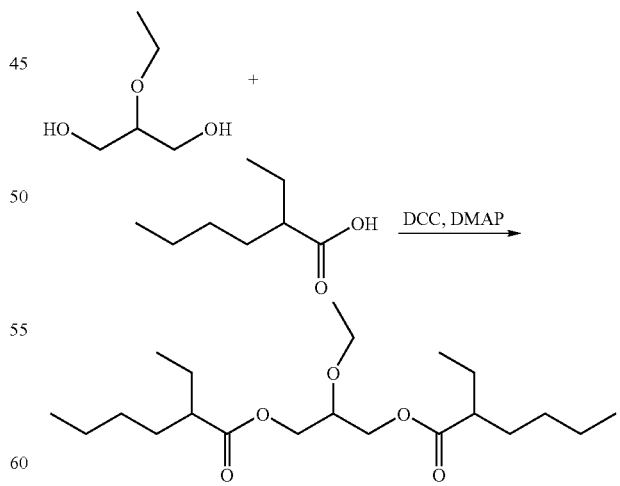

The same procedure was followed, which is for the preparation of Compound 11, starting from the diol of Compound 6 (5.6. g., 0.047 mol) to give Compound 12 as a light yellow liquid (10.2 g., 58%). $^1$H NMR (200 M Hz, CDCl$_3$): δ0.6-0.8 (m, 15H), 1.2-1.8 (m, 16H), 2.2-2.4 (m, 2H), 3.5-3.7 (m, 3H), 4.0-4.3 (m, 4H). TLC Analysis: 1:9 EtOAc:Hexane $R_f$ 0.7, UV active and α-naphthol charring.

M. Synthesis of 2-Ethyl Hexanoic Acid Ester of 2-propyl Glycerol (Compound 13)

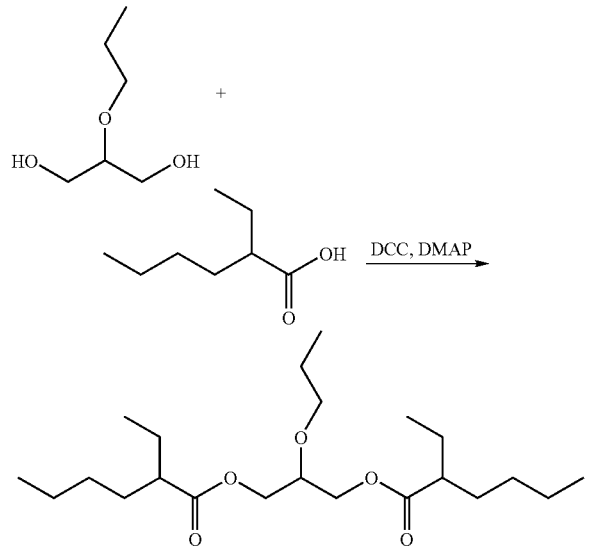

The same procedure was followed, which is for the preparation of Compound 11, starting from the diol of Compound 7, (1.5 g., 0.011 mol) to give Compound 13 (3 g., 70%) as a yellow liquid. $^1$H NMR (200 M Hz, CDCl$_3$): δ0.8-0.9 (m, 15H), 1.2-1.8 (m, 18H), 2.2-2.4 (m, 2H), 3.5-3.7 (m, 3H), 4.0-4.3 (m, 4H). TLC Analysis: 1:9 EtOAc:Hexane $R_f$ 0.7, UV active and α-naphthol charring.

N. Synthesis of bis(2,2'-1,3-dioxacyclohexyl)-5,5'-n-hexylether (Compound 14)

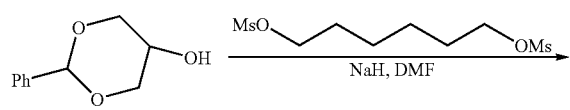

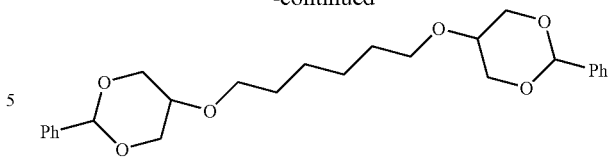

To a stirred solution of alcohol of Compound 1 (59 g., 0.328 mol) in dry DMF (200 mL) sodium hydride (15.76 g., 0.656 mol, 60% w/w in paraffin oil) was added at 0° C. After 45 min., methanesulfonic acid (CH$_3$SO$_3$H) diester of 1,6-hexanediol (45 g, 0.165 mol) was added at 0° C., reaction mixture was warmed to room temperature and stirred for 24 h. It was quenched with saturated aq. NH$_4$Cl solution (200 mL) at 0° C. and extracted with ethyl acetate (2×250 mL). The combined organic layers were washed with water (200 mL), brine (100 mL), dried (Na$_2$SO$_4$), concentrated and purified by column chromatography (60-120 Silica gel, 3:7 EtOAc:Hexane) to afford Compound 14 (8 g., 11%) as a solid melting point (DSC) 90° C. $^1$H NMR (200 M Hz, CDCl$_3$) δ1.2-1.8 (m, 8H), 4.0-4.4 (dd, 8H, J=8.3 Hz), 3.2-3.7 (m, 6H), 5.5 (s, 2H), 7.2-7.7 (m, 5H). TLC Analysis: 3:7 EtOAc:Hexane $R_f$ 0.6, UV active and α-naphthol charring.

Note: The DSC melting temperatures are determined by loading the solid sample at room temperature and heating to a temperature 20° C. above the melting temperature of the compound at 5° C./minute. The melting temperature of the compound is taken as the temperature where most of the compound (>90% of the area under the melting curve) is melted into liquid.

O. Synthesis of Tetrol Ether, Bis(1,3-hydroxypropyl)-2,2'-n-hexyl Ether (Compound 15)

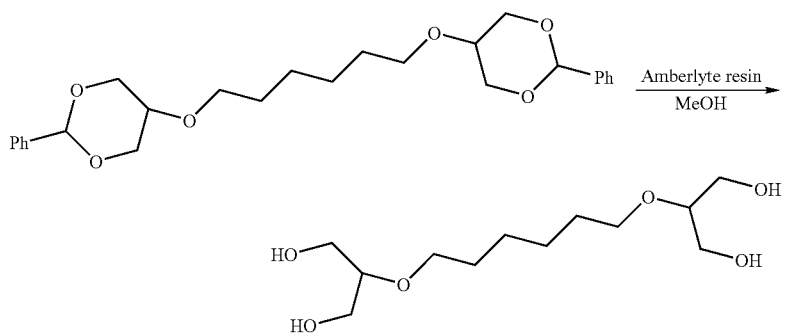

To a stirred solution of Compound 14 (4 g, 0.009 mol) in methanol (20 mL) amberlyte resin (0.5 g) was added and stirred at room temperature for 12 h. The reaction mixture was filtered and organic layer was concentrated and the residue purified through column chromatography (60-120 Silica gel, 1:2 EtOAc-Hexane) to give the tetrol of Compound 15 (1.75 g, 73%) as a solid. The solid has a melting point of (DSC) 74° C. IR (neat): 668, 756, 1214, 3020, 3682 cm$^{-1}$; $^1$H NMR (200 M Hz, CDCl$_3$) δ1.2-1.5 (m, 8H), 3.0-3.5 (m, 14H). TLC Analysis: 1:9 MeOH:CHCl$_3$ $R_f$ 0.1, α-naphthol charring.

Note: The DSC melting temperatures are determined by loading the solid sample at room temperature and heating to a temperature 20° C. above the melting temperature of the compound at 5° C./minute. The melting temperature of the compound is taken as the temperature where most of the compound (>90% of the area under the melting curve) is melted into liquid.

P. Synthesis of 2-ethyl Hexanoyl Tetra Ester of Compound 15, 2-ethyl Hexanoic Acid Ester of bis(1,3-dihydroxy Propyl)-2,2'-n Hexyl Ether (Compound 16)

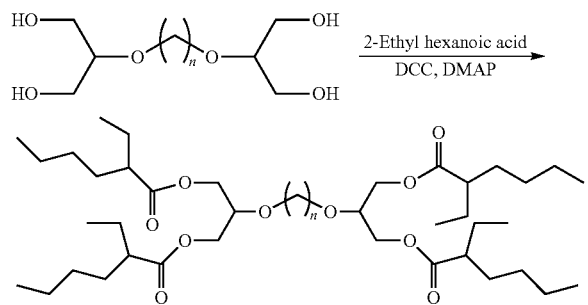

Tetrol, Compound 15 (0.3 g., 1.12 mmol) was dissolved in dichloromethane and to this was added DCC (0.92 g., 4.4 mmol) and stir it for 5 minutes. To this was added 2-ethyl hexanoic acid (0.63 g., 4.4 mmol) and DMAP (catalytic amount) at 0° C., stir it for 8 h at room temperature. The reaction mixture was filtered, washed with bicarbonate solution, and water. Solvent was evaporated to dryness to get pale yellow liquid (0.64 g., 68%). $^1$H NMR (200 M Hz, CDCl$_3$) δ0.85-0.91 (m) 1.23-1.42 (m) 1.53-1.63 (m) 2.2-2.4 (m) 3.5-3.6 (m) 4.1-4.4 (m) TLC Analysis: 3:7 EtOAc:Hexane R$^f$ 0.2, UV inactive and α-naphthol charring.

DSC behavior: No crystallization or melting was observed when cooled to −45° C. and heated to 25° C.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C./minute from −45° C. to 25° C.

Q. Synthesis of Trimethyl Glycerol or 1,2,3-trimethoxy Propane (Compound 17)

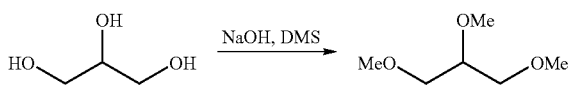

To a stirred solution of glycerol (100 g., 1.086 mol) in dry DMF (300 mL) sodium hydroxide (130.4 g., 3.26 mol) was added at 0° C. After 45 min dimethyl sulphate (DMS) (310 mL, 3.26 mol) was added at 0° C., reaction mixture was warmed to room temperature and stirred for 48 h. It was quenched with water (500 mL) at 0° C. and extracted with dichloromethane (2×500 mL). The combined organic layers were washed with water (200 mL), brine (100 mL), dried (Na$_2$SO$_4$) and concentrated to afford Compound 17 (29 g., 20%) as a colorless low viscosity liquid. $^1$H NMR (200 M Hz, CDCl$_3$) δ3.8-4.2 (m, 14H) TLC Analysis: 3:7 EtOAc:Hexane R$_f$ 0.5, α-naphthol charring.

R. Synthesis of 2-Tosyl 1,3-benzylidine Glycerol (Compound 18)

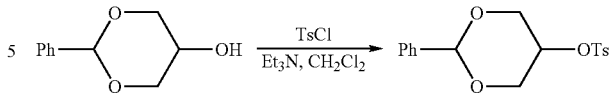

To a stirred and cooled (0° C.) solution of alcohol of Compound 1 (10 g., 0.055 mol) in dichloromethane (100 mL), Et$_3$N (15.4 mL, 0.11 mol) and tosyl chloride (12.5 g., 0.066 mol) were added sequentially. The reaction mixture was stirred at room temperature for 36 h and diluted with water (200 mL), extracted with dichloromethane (2×100 mL). The combined organic layers were washed with brine (100 mL), dried (Na$_2$SO$_4$), concentrated and the residue purified by column chromatography (60-120 Silica gel, 1:10 EtOAc:Hexane) to give Compound 18 (15 g., 81%) A light brown solid has a melting point (DSC) of 125° C. TLC Analysis: 1:1 EtOAc:Hexane R$_f$ 0.6, UV active and α-naphthol charring.

Note: The DSC melting temperatures are determined by loading the solid sample at room temperature and heating to a temperature 20° C. above the melting temperature of the compound at 5° C./minute. The melting temperature of the compound is taken as the temperature where most of the compound (>90% of the area under the melting curve) is melted into liquid.

S. Synthesis of 1,3-benzylidene Glycerol-2-azide (Compound 19)

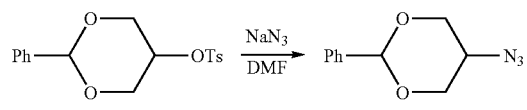

To a stirred solution of Compound 18 (15 g., 0.044 mol) in DMF (60 mL) at room temperature, NaN$_3$ (5.83 g., 0.089 mol) was added and stirred at reflux for 4 h. Reaction mass was quenched with water (150 mL) and extracted with ethyl acetate (2×250 mL). Combined organic layers were washed with brine (75 mL), dried (Na$_2$SO$_4$), concentrated to afford Compound 19 (9 g., quantitative) as a dark brown liquid. IR (neat): 1387, 1671, 2107, 3017 cm$^{-1}$; $^1$H NMR (200 M Hz, CDCl$_3$); δ3.5-3.8, 4.3-4.5 (m, 4H), 4.0-4.2 (m, 1H), 5.4 (s, 1H), 7.3-7.5 (m, 5H). TLC Analysis: 1:9 EtOAc:Hexane R$_f$ 0.6, UV active and α-naphthol charring.

T. Synthesis of 1,3-benzylideneglycerol-2-amine (Compound 20)

To a stirred solution of azide Compound 19 (11 g., 0.053 mol) in dry tetrahydrafuran (THF) (100 mL) lithium aluminum hydride (LAH) (3.39 g., 0.091 mol) was added at 0° C. and stirred at the same temperature for 1 h. Water (100 mL) followed by NaOH solution was added to the reaction mixture at 0° C. and stirred for 30 min and extracted with EtOAc (2×15 mL). The combined organic layers were washed with brine (100 mL), dried (Na$_2$SO$_4$), concentrated to afford Compound 20 (3 g, 31%) as a yellowish liquid $^1$H NMR (200 M Hz, CDCl$_3$); δ1.2 (brs, 2H), δ3.2-3.4 (m, 1H), 3.3-3.5 (m, 2H), 4.2-4.4 (m, 2H), 5.4 (s, 1H), 7.2-7.6 (m, 5H). TLC Analysis: 1:9 MeOH:CHCl$_3$ R$_f$ 0.4, UV active and α-naphthol charring.

U. Synthesis of Serinol (Compound 21)

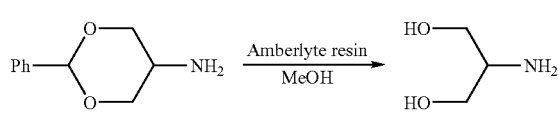

To a stirred solution of Compound 20 (1 g., 0.0062 mol) in methanol (10 mL) amberlyte resin (0.2 g.) was added and stirred at room temperature for 12 h. The reaction mixture was filtered and organic layer was concentrated but the compound was bound with the acidic resin, so the resin in methanol was basified by passing $NH_3$ gas and filtered and concentrated to get the pure amine Compound 21 (0.3 g., 53%) as a gummy syrup. $^{13}C$ NMR (50 M Hz, $CDCl_3$): 54, 63

TLC Analysis: 1:9 MeOH:$CHCl_3$ $R_f$ 0.0, ninhydrin charring.

V. Synthesis of Substituted Triazole (Compound 22)

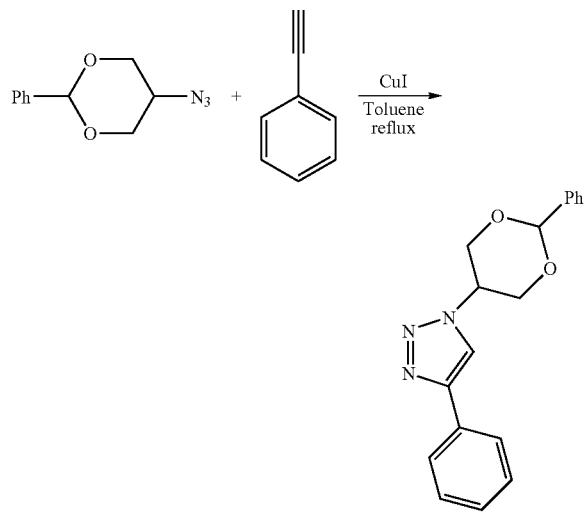

To a stirred solution of phenyl acetylene (0.1 g., 0.97 mmol) and cuprous iodide (0.185 g., 0.97 mmol) in toluene (10 ml) was added glycerol azide (0.2 g., 0.97 mmol) and refluxed for 20 h. The precipitated product was extracted with ethyl acetate (3×5 ml) and the organic extract was dried. The crude product was purified by column chromatography to yield 1,4-isomer (0.265 g., 85%). The product was characterized by NMR and IR. $^1H$ NMR (200 M Hz, $CDCl_3$) δ4.3-4.7 (m, 4H), 4.9 (m, 1H), 5.7 (s, 1H), 7.2-7.9 (m, 10H). The triazole purified by column chromatography is a solid with a melting temperature of 215° C. TLC Analysis: 2:3 EtOAc:Hexane $R^f$ 0.66, UV, iodine active, α-naphthol charring.

To a stirred solution of triazole, Compound 22 (1.0 g., 3.2 mmol) in methanol (15 mL) amberlyte resin (0.1 g.) was added and stirred at room temperature for 12 h. The reaction mixture was filtered and organic layer was concentrated and the residue was purified by column chromatography (60-120 Silica gel, 1:2 EtOAc-Hexane) to give the corresponding diol (0.6 g., 85%) as a pale yellow viscous liquid IR (neat): 766.58, 1000.72, 1505.85, 2357.52, 2885.46, 2923.63, 3351.89 $cm^{-1}$ $^1H$ NMR (200 M Hz, $CDCl_3$) δ1.5 (brs, 1H), 3.0 (brs, 1H), 4.0-4.3 (m, 4H), 4.65 (m, 1H), 7.3-7.5 (m, 5H), 7.7 (s, 1H). TLC Analysis: 1:1 EtOAc:Hexane $R^f$ 0.1, α-naphthol charring.

W. Synthesis of Polyester (Polymer 1)

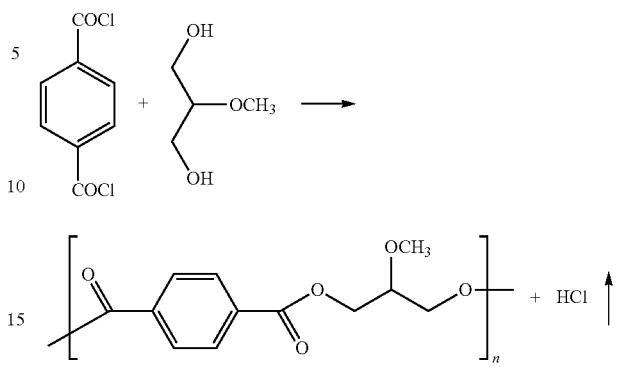

Procedure: A 100 mL of three neck flask equipped with a nitrogen inlet tube extending below the surface of the reaction mixture, a mechanical stirrer, and an exit tube for nitrogen and evolved hydrogen chloride is flushed with nitrogen and charged first with 20 g. (0.099 mol) terephthaloyl chloride followed by 10.3 g. (0.099 mol) 2-methoxy-1,3-propanediol (MPDO). The heat of the reaction causes the acid chloride to melt. The reaction is stirred vigorously and nitrogen is passed through the reaction to avoid accumulation of hydrogen chloride, which may bring about formation of tars. In about 1 hr., the evolution of hydrogen chloride slowed considerably and the mixture began to solidify. The temperature of the reaction mixture is then raised to 180° C. by means of an oil bath and held at that temperature for 1 hr. During the last ten minutes of the 180° C. heating cycle the last of the HCl is removed by reducing the pressure to 0.5-1.0 mm.

The polymer is obtained as a black solid. The amorphous solid melting point and solubility were checked. The solid was dissolved in $CHCl_3$ and made a dry film by evaporating the solvent after casting a layer on a glass plate.

X. Synthesis of Polyester (Polymer 2)

To a round bottomed flask equipped with magnetic stirrer were charged terephthaloyl dichloride (0.404 g., 1.99 mmol), 1,3-propane diol (PDO) (0.152 g. 2.0 mmol) and tetrahydrofuran (25 ml) dried from sodium and benzophenone. Polymerization was initiated by drop wise addition of a stoichiometric amount of triethylamine (0.202 g., 2.0 mmol) over 30 minutes. The mixture was stirred for 3 hours at room temperature. The solution was slowly warmed to ambient temperature and left at that temperature for 24 hr and the final polymer was precipitated in excess water. The solution was washed with sodium bicarbonate to remove any unreacted acid. The isolated polymer was thoroughly washed with methanol and dried at 60° C. under vacuum to constant weight (84% yield). The polymer had inherent viscosity of 0.36 dl/0.5 g. in o-chlorophenol. The melting point of the homo polyester as determined from Differential Scanning Calorimeter (DSC) is 230° C.

Y. Synthesis of Copolyester (Polymer 3)

To a round bottomed flask equipped with magnetic stirrer were charged terephthaloyl dichloride (0.404 g., 1.99 mmol), 1,3-propane diol (PDO) (0.106 g. 1.39 mmol), 2-methoxy-1,3-propane diol (MPDO) (0.064 g., 0.604 mmol) and tetrahydrofuran (25 ml) dried from sodium and benzophenone. Polymerization was initiated by drop wise addition of a stoichiometric amount of triethylamine (0.202 g., 2.0 mmol) over 30 minutes. The mixture was stirred for 3 hours at room temperature. The solution was slowly warmed to ambient temperature and left at that temperature for 24 hr and the final polymer was precipitated in excess water. The solution was washed with sodium bicarbonate to remove any unreacted acid. The isolated polymer was thoroughly washed with methanol and dried at 60° C. under vacuum to constant weight (75% yield). The polymer had inherent viscosity of 0.18 dl/0.5 g. in o-chlorophenol. The melting point of the copolyester as determined from Differential Scanning Calorimeter (DSC) is 184° C.

Z. Synthesis of Copolyester (Polymer 4)

To a round bottomed flask equipped with magnetic stirrer were charged terephthaloyl dichloride (0.404 g., 1.99 mmol), 1,3-propane diol (PDO) (0.072 g., 0.947 mmol), 2-methoxy-1,3-propane diol (MPDO) (0.111 g., 1.05 mmol) and tetrahydrofuran (25 ml) dried from sodium and benzophenone. Polymerization was initiated by drop wise addition of a stoichiometric amount of triethylamine (0.202 g., 2.0 mmol) over 30 minutes. The mixture was stirred for 3 hours at room temperature. The solution was slowly warmed to ambient temperature and left at that temperature for 24 hr and the final polymer was precipitated in excess water. The solution was washed with sodium bicarbonate to remove any unreacted acid. The isolated polymer was thoroughly washed with methanol and dried at 60° C. under vacuum to constant weight (68% yield). The polymer had a number average molecular weight of 13,500 (molecular weight dispersity of 2.3). The melting point of the copolyester as determined from Differential Scanning Calorimeter (DSC) is 148° C.

AA. Synthesis of Polyester (Polymer 5)

To a round bottomed flask equipped with magnetic stirrer were charged terephthaloyl dichloride (0.404 g., 1.99 mmol), 2-methoxy-1,3-propane diol (MPDO) (0.21 g., 1.99 mmol) and tetrahydrofuran (25 ml) dried from sodium and benzophenone. Polymerization was initiated by dropwise addition of a stoichiometric amount of triethylamine (0.202 g., 2.0 mmol) over 30 minutes. The mixture was stirred for 3 hours at room temperature. The solution was slowly warmed to ambient temperature and left at that temperature for 24 hr and the final polymer was precipitated in excess water. The solution was washed with sodium bicarbonate to remove any unreacted acid. The isolated polymer was thoroughly washed with methanol and dried at 60° C. under vacuum to constant weight (79% yield). The polymer had a number average molecular weight of 12,550 (molecular weight dispersity of 2.1) The glass transition of the homo polyester as determined from Differential Scanning Calorimeter (DSC) is 15° C. The transitions were recorded after the second heating cycle in order to minimize the plasticization due to moisture in the polymer. For example in polymer-4 showed a second order transition at 12° C. during the first heating cycle. Upon subjecting the sample to second heating cycle, a glass transition temperature, Tg, was observed at 15° C.

The properties of polyesters and copolyesters (Polymers 2-5) are summarized in Table 5 below.

TABLE 5

Properties of Polyesters and Copolyesters

| Poly. # | TC g. | PDO g. | MPDO g. | Yield | Viscosity dl/g. | $M_n$ | Mol. Wt. MWD | MP ° C. |
|---|---|---|---|---|---|---|---|---|
| Poly. 2 | 0.404 | 0.152 | — | 84 | 0.36* | — | — | 230 |
| Poly. 3 | 0.404 | 0.106 | 0.064 | 75 | 0.18* | — | — | 184 |
| Poly. 4 | 0.404 | 0.072 | 0.105 | 68 | — | 13500 | 2.3 | 148 |
| Poly. 5 | 0.404 | — | 0.210 | 79 | — | 12550 | 2.1 | 15** |

*Inherent viscosity was measured in o-chlorophenol
**glass transition temperature
TC = terephthloyl chloride,
PDO = 1,3 propane diol,
MPDO = 2-methoxy-1,3-propane diol.
$M_n$ = no. average molecular weight,
MWD = molecular weight distribution.

TC=terphthloyl chloride, PDO=1,3 propane diol, MPDO=2-methoxy-1,3-propane diol.

$M_n$=no average molecular weight, MWD=molecular weight distribution.

Differential scanning calorimetry (DSC) (heating rate 10° C./min) was used to determine the first and second order transition in polymers. Samples are heated under a nitrogen atmosphere at a rate of 10° C./minute to 300° C., programmed cooled back to −30° C. and then reheated to 300° C. at a rate of 10° C./min. The observed sample glass transition temperature (Tg), and crystalline melting temperature, ($T_m$), noted were from the second heat in order to minimize the plasticization due to moisture in the polymer. For example, Polymer 5 showed a second order transition at 12° C. during the first heating cycle. Upon subjecting the sample to second heating cycle, a glass transition temperature, (Tg), was observed at 15° C.

1H NMR for PPT:
Aromatic protons~8.1-8.3 ppm; methylene protons adjacent to the ester groups~4.7 ppm; center methylene protons in trimethylene~2.3 ppm.

1HNMR for MPPT:
Aromatic protons~8.1-8.3 ppm; methylene protons adjacent to the ester groups~4.7 ppm, center methine proton attached to methoxy~4.0 ppm and methoxy protons~3.7 ppm BB. Synthesis of Polyurethane (Polymer 6)

A solution containing 0.106 g. (0.001 mol) of 2-methoxypropane-1,3-diol and 0.151 g. (0.0009 mol) of hexamethylene isocyanate and a drop of dibutyltin dilaurate in 3 ml of dry tetrahydrofuran was stirred at room temperature for 6 hr. To the solution was added 0.0116 g. (0.0001 mol) of 2-hydroxyethyl acrylate. The progress of the reaction was monitored by IR. The solution was mixed with IRGACURE® 651 photoinitiator, (2,2'-dimethoxy-2-phenylacetophenone) which is a alpha cleavage type photoinitiator activated under black light. A film was cast on the glass slide. After the solvent was evaporated, the soft film was covered with a release liner and irradiated under black light for five minutes. A tack-free, transparent, and solvent resistant film was obtained. The reaction scheme is given below:

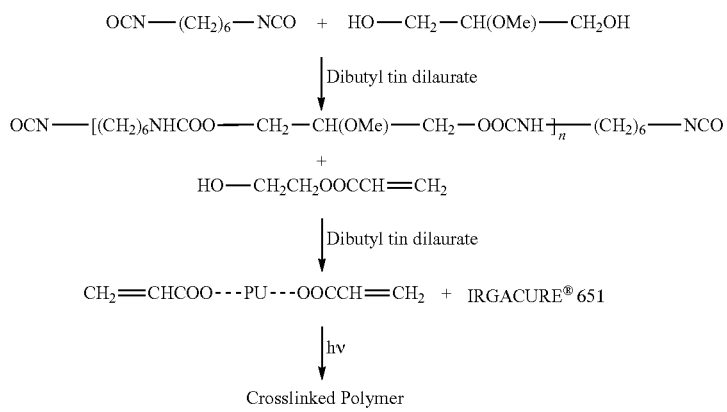

PU = Polyurethane

CC. Synthesis of Polyurethane (Polymer 7)

A solution containing 0.106 g. (0.001 mol) of 2-methoxypropane-1,3-diol and 0.151 g. (0.0009 mol) of hexamethylene isocyanate and a drop of dibutyltin dilaurate in 3 ml of dry tetrahydrofuran was stirred at room temperature for 6 hr. To the solution was added 0.0223 g. (0.0001 mol) of aminopropyltriethoxysilane. The progress of the reaction was monitored by IR. The solution was cast on a glass slide. After the solvent was evaporated, the film was allowed to hydrolyze and crosslink in air. A tack-free, transparent, and solvent resistant film was obtained after 24 hr. The reaction scheme is given below:

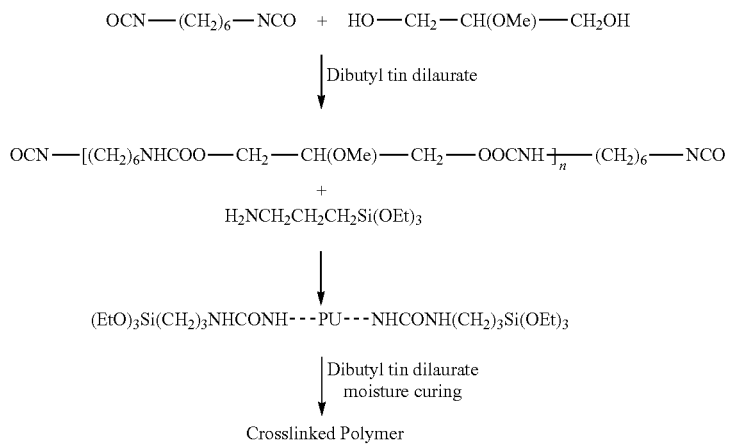

PU = Polyurethane

DD. Synthesis of 1,3-benzylidene Glyceryl-2-acrylate (Compound 23)

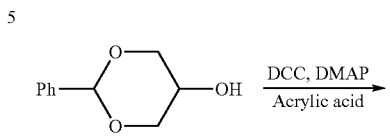

-continued

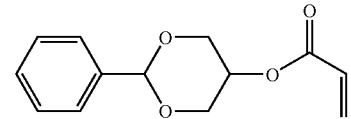

To a stirred solution of acrylic acid (0.76 mL, 0.01 mol) in dry dichloromethane (5 mL), DCC (2.28 g., 0.022 mol), followed by alcohol of Compound 1 (2 g., 0.01 mmol) and DMAP (1.35 g., 0.01 mol) were added at 0° C. and stirred for 24 h at room temperature. Reaction mass was filtered and filtrate was washed with NaHCO$_3$ solution and water.

Organic layers were washed with brine (10 mL), dried (Na$_2$SO$_4$) and concentrated. The crude residue was purified by column chromatography (60-120 Silica gel, 1:20 EtOAc: Hexane) to afford Compound 22 (0.2 g., 8%) as a solid with melting temperature of 99° C. $^1$H NMR (200 M Hz, CDCl$_3$): δ4.1-4.4 (dd, 4H, J=7.1 Hz), 4.8 (m, 1H), 5.5 (s, 1H), 5.8-5.9 (m, 1H), 6.2-6.3 (m, 1H), 6.4-6.58 (m, 1H), 7.3-7.5 (m, 5H). TLC Analysis: 3:7 EtOAc:Hexane R$_f$ 0.7, UV active and α-naphthol charring.

EE. Synthesis of Polyacrylate (Polymer 8a)

A 100 ml amber glass bottle was charged with 10 g of compound 23, 50 g. of methyl ethyl ketone and 0.02 g. azobis (iso-butyronitrile). The solution was flushed with nitrogen to expel dissolved oxygen. The bottle was sealed and shaken at 55° C. for 21 hours. The polymer was isolated from the viscous solution by precipitating in hexane. The isolated polymer was dried to constant weight under vacuum at 60° C.

FF. Synthesis of Polyacrylate (Polymer 8b)

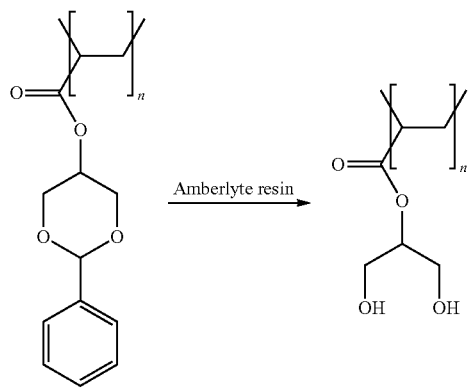

To a stirred solution of polymerized Compound 23 (5 g., 0.02 mol) in methanol/dichloromethane 50/50 (20 mL) amberlyte resin (0.5 g.) was added and stirred at room temperature for 12 h. The reaction mixture was filtered and organic layer was concentrated and the residue purified through column chromatography (60-120 Silica gel, EtOAc) to give polyhydroxyacrylate (2 g., 60%) as a solid.

GG. Synthesis of Glycerol-2-acrylate (Compound 24)

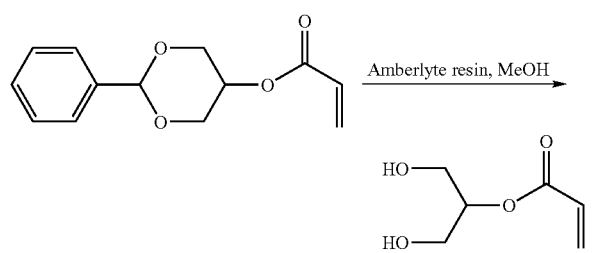

To a stirred solution of Compound 23 (5 g., 0.02 mol) in methanol (20 mL) amberlyte resin (0.5 g.) was added and stirred at room temperature for 12 h. The reaction mixture was filtered and organic layer was concentrated and the residue purified through column chromatography (60-120 Silica gel, 1:2 EtOAc-Hexane) to give the diol of Compound 23 (1.8 g., 58%) as a semi solid. $^1$H NMR (200 M Hz, CDCl$_3$) δ3.6-4.4 (m, 5H), 5.9 (d, 1H, J=6.5 Hz), 6.1-6.3 (m, 1H), 6.5 (d, 1H, J=7.8 Hz). TLC Analysis: 1:9 MeOH:CHCl$_3$ R$_f$ 0.3, UV active and α-naphthol charring.

Polymerization of Compound 24 can be affected by dissolving in methyl ethyl ketone in the presence of azobis(isobutyronitrile) by adopting a procedure similar to the preparation of Polymer 8a.

HH. Synthesis of 1,3-benzylidene Glyceryl-2-ethylvinyl Ether (Compound 25)

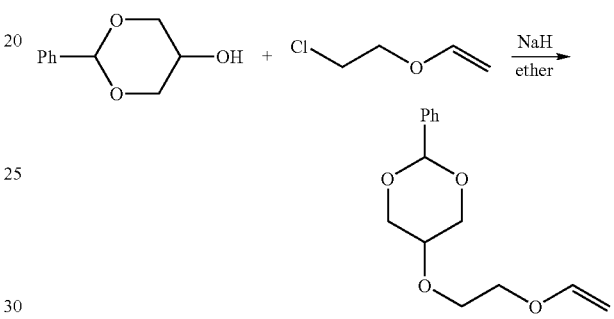

To a stirred solution of Compound 1 (1 g., 0.05 mol) in ether (4 ml) was added sodium hydride (0.24 g., 0.011 mol) at 0° C. and stirred at same temperature for 10 minutes and then was added chloroethylvinylether (0.84 ml, 0.0085 mol) and continued stirring for 48 h. The reaction mixture was quenched with NH$_4$Cl (10 ml) and extracted with ethylacetate. The organic layer was dried (Na$_2$SO$_4$) and concentrated. The crude residue was purified by column chromatography (60-120 Silica gel, 2:8 EtOAc: Hexane) to afford Compound 28 (0.52 g., 34.8%) as a viscous liquid. $^1$H NMR (200 M Hz, CDCl$_3$) δ3.4 (m, 1H), 3.8-4.2 (m, 8H), 4.4 (m, 2H), 5.5 (s, 1H), 6.4-6.5 (m, 1H), 7.3-7.6 (m, 5H).

TLC Analysis: 2:8 EtOAc: n-Hexane R$_f$ 0.4, UV active and α-naphthol charring.

DSC behavior: No crystallization or melting was observed when cooled to −45° C. and heated to room temperature.

Note: The DSC thermal behavior of this compound is determined by loading the compound at room temperature (25° C.). Cool the compound at 2.5° C./minute to −45° C. Kept at −45° C. isothermal for 10 minutes. Heated at 5° C. minute from −45° C. to 25° C.

II. Synthesis of Polyvinyl Ether (Polymer 9a)

Cationic polymerization of Compound 25 was carried out under dry nitrogen in a vessel equipped with three-way stopcock. The flask was charged with 10 g. of Compound 25 in 100 ml of toluene. The flask was cooled to −78° C. The reaction was initiated with by adding an initiator solution (hydrogen iodide and iodine solution) into the monomer solution. After the reaction was complete, the viscous solution was precipitated in prechilled ammonical methanol. The quenched reaction mixture was washed with excess methanol. The isolated polymer was dried under vacuum to constant weight.

JJ. Synthesis of Polyhydroxyvinylethers (Polymer 9b)

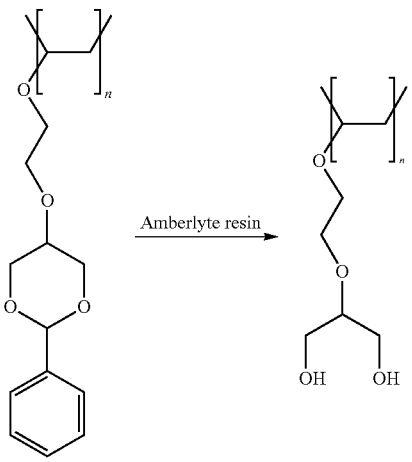

The polymerized vinylether protecting group in 9a, benzylidene is removed by adopting the procedure similar to the synthesis of polymer 8b.

KK. Synthesis of Compound 26

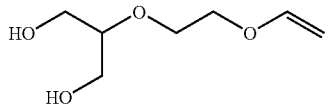

Compound 26 can be produced from Compound 25 by treating with acid or acidic resin as described for the compounds 5-7. These vinyl ethers can be polymerized either with diacid or diisocyanate groups to produce polyesters and polyurethane respectively with a pendant vinyl ether group. The pendant vinyl ether polymers can be used to cross link the polymers under cationic conditions.

Although the present invention has been described with reference to particular embodiments, persons skilled in the art will recognize that changes may be made in form and detail without departing from the spirit and scope of the invention. All references cited throughout the specification are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A polyester which is the condensation product of one or more of terephthalic acid, or a diacid having the structure HOOC—$(CH_2)_n$—COOH or a halide thereof or diester thereof and

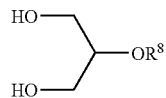

wherein $R^8$ is an alkyl group.

2. A polyester which is the condensation product of one or more of terephthalic acid, or a diacid having the structure HOOC—$(CH_2)_n$—COOH or a halide thereof or diester thereof and

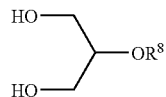

wherein $R^8$ is an alkyl group, wherein the diacid is HOOC$(CH_2)_n$COOH, wherein n is 0 to 20.

3. The polyester of claim 2, wherein n is 2 to 8.

4. The polyester of claim 1, wherein $R^8$ is a methyl, ethyl, propyl, butyl, pentyl or hexyl group.

5. The polyester of any one of claims 1 through 4, wherein the molecular weight of the polyester is greater than 500 grams/mole.

6. The polyester of any one of claims 1 through 4, wherein the molecular weight of the polyester is between about 500 and 100,000 grams/mole.

7. The polyester of any one of claims 1 through 4, wherein the molecular weight of the polyester is between about 500 and about 80,000 grams/mole.

8. A polyester which is the condensation product of one or more of terephthalic acid, or a diacid having the structure HOOC—$(CH_2)_n$—COOH or a halide thereof or diester thereof and

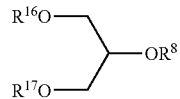

wherein $R^8$ is an alkyl group, wherein a terminal hydroxyl group of the polyester is derivatized with a methacrylate, an acrylate a hydrolysable alkoxysilane, a photoinitiator or combination thereof.

9. A polyurethane which is the condensation product of a diisocyanate and

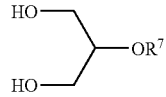

wherein $R^7$ is an alkyl, substituted alkyl, aryl or substituted aryl group.

10. The polyurethane of claim 9, wherein $R^7$ is methyl, ethyl, propyl, butyl, pentyl or hexyl group.

11. The polyurethane of either claim 9 or 10, wherein the molecular weight of the polyurethane is greater than 500 grams/mole.

12. The polyurethane of either claim 9 or 10, wherein the molecular weight of the polyurethane is between about 500 and about 150,000.

13. The polyurethane of either claim 9 or 10, wherein the molecular weight of the polyurethane is between about 1,000 and about 100,000.

14. The polyurethane of claim 9 or 10, wherein a terminal hydroxyl group of the polyurethane is derivatized with a methacrylate, an acrylate or a vinyl ether or hydrolysable alkoxysilanes or a photoinitiator.

* * * * *